United States Patent [19]
Waterson et al.

[11] Patent Number: 6,093,718
[45] Date of Patent: Jul. 25, 2000

[54] SUBSTITUTED PYRIMIDINE DERIVATIVES AND THEIR PHARMACEUTICAL USE

[75] Inventors: David Waterson; Elaine Sophie Elizabeth Stokes; George Robert Brown; Nicholas John Newcombe, all of Macclesfield, United Kingdom

[73] Assignee: Zeneca Limited, London, United Kingdom

[21] Appl. No.: 09/242,309

[22] PCT Filed: Jul. 25, 1997

[86] PCT No.: PCT/GB97/02029

§ 371 Date: Feb. 12, 1999

§ 102(e) Date: Feb. 12, 1999

[87] PCT Pub. No.: WO98/06705

PCT Pub. Date: Feb. 19, 1998

[30] Foreign Application Priority Data

Aug. 14, 1996 [GB] United Kingdom .................. 9617060
Feb. 14, 1997 [GB] United Kingdom .................. 9703027

[51] Int. Cl.[7] .......................... A01N 43/54; A01N 43/58; A01N 43/40; C07D 403/00; C07D 239/02
[52] U.S. Cl. .......................... 514/256; 514/252; 514/256; 514/269; 514/274; 514/275; 544/238; 544/295; 544/296; 544/298; 544/311; 544/317; 544/319; 544/320; 544/321; 544/323; 544/326; 544/327; 544/329
[58] Field of Search ........................ 514/252, 256, 514/269, 275, 274; 544/295, 317, 319, 320, 326, 327, 238, 296, 311, 321, 323, 329, 298

[56] References Cited

U.S. PATENT DOCUMENTS

| | | | |
|---|---|---|---|
| 4,167,567 | 9/1979 | McCall | 424/250 |
| 4,231,938 | 11/1980 | Monaghan et al. | 260/345.5 |
| 4,537,896 | 8/1985 | Claeson et al. | 514/330 |
| 4,788,196 | 11/1988 | Cross et al. | 514/252 |
| 4,806,536 | 2/1989 | Cross et al. | 514/252 |
| 5,138,058 | 8/1992 | Geisen et al. | 544/295 |
| 5,332,822 | 7/1994 | Misra | 546/164 |
| 5,371,091 | 12/1994 | Misra et al. | 514/314 |
| 5,411,978 | 5/1995 | Edmonds-Alt et al. | 514/318 |
| 5,563,141 | 10/1996 | Wayne et al. | 514/252 |
| 5,580,881 | 12/1996 | Binet et al. | 514/307 |
| 5,606,065 | 2/1997 | Emonds-Alt et al. | 546/223 |
| 5,856,326 | 5/1999 | Anthony et al. | 514/252 |

FOREIGN PATENT DOCUMENTS

| | | |
|---|---|---|
| 10177/92 | 7/1992 | Australia . |
| 0 097 630 A2 | 1/1984 | European Pat. Off. . |
| 0 232 740 A1 | 8/1987 | European Pat. Off. . |
| 0 233 051 | 8/1987 | European Pat. Off. . |
| 0 244 115 | 11/1987 | European Pat. Off. . |
| 0 308 337 | 3/1989 | European Pat. Off. . |
| 0 324 421 A2 | 7/1989 | European Pat. Off. . |
| 0 359 389 | 3/1990 | European Pat. Off. . |
| 0 352 946 A1 | 10/1990 | European Pat. Off. . |
| 0 409 413 | 1/1991 | European Pat. Off. . |
| 0 495 750 | 7/1992 | European Pat. Off. . |
| 0 515 240 A1 | 11/1992 | European Pat. Off. . |
| 0 519 449 A1 | 12/1992 | European Pat. Off. . |
| 0 555 824 A1 | 8/1993 | European Pat. Off. . |
| 0 576 941 A1 | 1/1994 | European Pat. Off. . |
| 0 608 759 A2 | 8/1994 | European Pat. Off. . |

(List continued on next page.)

OTHER PUBLICATIONS

Bowers Nemia et al., "Synthetic Routes to 3–Pyrrolidinol", Synth. Comm., 13(13):1117–1123 (1983).

Budavari: Merck Index, vol. 11 ED., 1989, See Monograph Nos. 804 and 2807.

Cattel et al: "Drug design based on biosynthetic studies: synthesis, biological activity, and kinetics of new inhibitors of 2,3–oxidosualene cyclase and squalene epoxidase.", Steroids., vol. 53, No. 3–5, 1989, pp. 363–391, XP000611661.

Chambers et al., "Preparation of arylpyridine compounds for treating leukotriene–related diseases", Chemical Abstracts, Abstract No. 139113, vol. 119 (1993).

Cross et al., "Preparation of N–[(heterocyclicylmethoyx)phenyl] sulfamides and analogs as antiarrhythmics", Chemical Abstracts, Abstract No. 231211, vol. 113 (1989).

E. Jucker, "Über C–substituierte Piperazinderativate", Helv. Chim. Acta., 45:2383–2042 (1962).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. [1)] Reactions of Acetoacetamide and β–Aminocrotonamide with β–Diketone, β—Ketoaldehyde and Related Compounds", Chem. Pharm. Bull., 24(2):303–309 (1976).

Kettner et al., "The Selective Inhibition of Thrombin by Peptides of Boroarginine", The Journal of Biological Chemistry, vol. 265, No. 30, pp. 18289–18297 (1990).

Mitsunobu et al., "Preparation of Carboxylic Esters and Phosphoric Esters by the Activation of Alcohols", Bull. Chem. Soc. Jpn., 44(12):3427–3430 (1971).

Smith et al., "Fibrin, Red Cell and Platelet Interactions in an Experimental Model of Thrombosis", Br. J. Pharmac., vol. 77, pp. 29–38 (1982).

(List continued on next page.)

*Primary Examiner*—Mukund J. Shah
*Assistant Examiner*—Ben Schroeder
*Attorney, Agent, or Firm*—Pillsbury Madison & Sutro, LLP Intellectual Property Group

[57] ABSTRACT

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

11 Claims, No Drawings

FOREIGN PATENT DOCUMENTS

| | | |
|---|---|---|
| 2 697 252 A1 | 4/1994 | France . |
| 39 05 364 A1 | 8/1990 | Germany . |
| 42 43 858 A1 | 6/1994 | Germany . |
| 43 06 506 A1 | 9/1994 | Germany . |
| 1 449 100 | 9/1976 | United Kingdom . |
| WO 92/08709 | 5/1992 | WIPO . |
| 92/18478 | 10/1992 | WIPO . |
| WO 93/06085 | 4/1993 | WIPO . |
| WO 94/18185 | 8/1994 | WIPO . |
| WO 94/20467 | 9/1994 | WIPO . |
| WO 94/20468 | 9/1994 | WIPO . |
| WO 94/22835 | 10/1994 | WIPO . |
| WO 96/05189 | 2/1996 | WIPO . |
| 96/10022 | 4/1996 | WIPO . |
| 96/226196 | 8/1996 | WIPO . |
| 96/30343 | 10/1996 | WIPO . |
| 97/06802 | 2/1997 | WIPO . |
| WO97/06802 | 7/1997 | WIPO . |
| WO 97/28128 | 8/1997 | WIPO . |
| WO 97/28129 | 8/1997 | WIPO . |
| WO 97/30971 | 8/1997 | WIPO . |
| WO 98/06705 | 2/1998 | WIPO . |

OTHER PUBLICATIONS

Szmant et al., "Concerning the Variable Character of the Sulfone Group", J. Amer. Chem. Soc., vol. 78, pp. 3400–3403 (1956).

Tabacik et al: "Squalene expoxidase, oxido–squalene cyclase and cholesterol biosynthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

Vigroux e tal., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Produrgs of Acetamiophen", J. Med. Chem., vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Wallis, "Inhibitors of Coagulation Factor Xa: From Macromolecular Beginnings to Small Molecules", Current Opinion in Therapeutic Patents, Aug., 1993, pp. 1173–1179.

SUBSTITUTED PYRIMIDINE DERIVATIVES AND THEIR PHARMACEUTICAL USE

This application is a 371 of PCT/GB 97/02029, filed Jul. 25, 1997.

This invention concerns heterocyclic derivatives which are useful in inhibiting oxido-squalene cyclase. processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

There is evidence that high serum cholesterol levels are an important risk factor in coronary heart disease and associated diseases such as atherosclerosis and ischemic heart disease. As a result there has been a great deal of interest in finding ways of lowering cholesterol levels in blood plasma. Although it has been possible to obtain some reduction by means of diet, only modest reductions have been obtained by controlling the dietary intake of cholesterol. Consequently, there is a need for therapeutic approaches to reducing cholesterol levels.

Several different classes of compounds have been reported to possess the capability of lowering cholesterol levels in blood plasma. For example agents which inhibit the enzyme HMGCoA reduces, which is essential for the production of cholesterol, have been reported to reduce levels of serum cholesterol. Illustrative of this class of compounds is the HMGCoA reductase inhibitor known as lovastatin which is disclosed in U.S. Pat. No. 4,231,938. Other agents which are reported to lower serum cholesterol include those which work by complexing with bile acids in the intestinal system, called "bile acid sequestrants". By lowering the levels of bile acid circulating in the enterohepatic system replacement of bile acids by synthesis in the liver from cholesterol is promoted. This results in an upregulation of the hepatic LDL cholesterol receptor and as a consequence a lowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interrupt cholesterol biosynthesis and give rise to a lowering of cholesterol levels in blood plasma.

The present invention is based on the discovery that certain heterocyclic derivatives are inhibitors of oxido-squalene cyclase and are hence useful in treating diseases and medical conditions in which inhibition of oxido-squalene cyclase is desirable.

According to the present invention there is provided a compound of formula I (set out hereinafter together with the other formulae referred to herein on a separate sheet following the examples), or a pharmaceutically acceptable salt thereof, wherein:

$T^1$ is selected from N and CR, wherein R may be hydrogen, (1–4C)alkyl, (2–4C)alkenyl, (2–4C)alkynyl;

$R^1$ is hydrogen, amino, halogeno, cyano, (1–6C)alkyl (1–6C)alkylamino, (1–6C)dialkylamino or (1–6C) alkoxy;

m is 1 or 2;

$T^2$ is selected from CH and N;

$T^3$ is selected from N and CR wherein R is as defined above; provided that when $T^2$ is CH then $T^3$ is not CR and when $T^1$ is CR then $T^3$ is not CR;

a and b are independently selected from 2 and 3;

c and d are independently selected from 1 and 2;

wherein the heterocyclic ring containing $T^1$ and the heterocyclic ring containing $T^2$ may, independently, be optionally substituted by one or more substituents selected from (1–6C) alkyl, (1–6C)alkoxy, phenyl(1–4C)alkyl, halogeno and (1–6C)alkoxycarbonyl;

X is selected from O, CO, S, SO, $SO_2$ and $CH_2$;

Q is selected from phenyl, naphthyl, phenyl(2–6C)alkenyl and a heteroaryl moiety which comprises a 5- or 6-membered monocyclic heteroaryl ring containing up to 3 heteroatoms selected from the group consisting of oxygen, nitrogen and sulphur and wherein Q may be unsubstituted or may bear one or more substituents selected from halogeno. hydroxy. amino. nitro, cyano. carboxy, carbamoyl, (1–6C) alkyl, (2–6C)alkenyl, (2–6C)alkynyl, (1–6C)alkoxy, (3–6C) cycloalkyl, (3–6C)cycloalkyl(1–4C)alkyl, (1–4C) alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C) alkylthio, (1–6C)alkylsulfinyl, (1–6C)alkylsulphonyl, halogeno(1–6C)alkyl, (1–6C)alkanoyl and tetrazolyl.

The compounds of the present invention are oxido-squalene cyclase inhibitors and hence possess the property of inhibiting cholesterol biosynthesis. Accordingly, there is provided a compound of formula I, or a pharmaceutically acceptable salt thereof. for use in medical therapy. There is also provided the use of a compound of formula I, or a pharmaceutically acceptable salt thereof. for the manufacture of a medicament for inhibiting oxido-squalene cyclase and in particular inhibiting cholesterol biosynthesis. Thus the compounds of the present invention will be useful in treating diseases or medical conditions in which an inhibition of oxido-squalene cyclase is desirable, for example those in which a lowering of the level of cholesterol in blood plasma is desirable. In particular, the compounds of the present invention will be useful in treating hypercholesterolemia and/or ischaemic diseases associated with atheromatous vascular degeneration such as atherosclerosis. As inhibitors of cholesterol biosynthesis, the compounds of the present invention will also be useful in treating fungal infections.

Thus according to a further feature of the present invention there is provided a method of inhibiting oxido-squalene cyclase in a warm-blooded animal (such as man) requiring such treatment, which method comprises administering to said animal an effective amount of a compound of formula I, or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I, or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

In particular the compounds of the present invention are potentially useful in inhibiting cholesterol biosynthesis in man and hence in treating the above-mentioned medical conditions in man.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art, for example by, resolution of a racemic form, by synthesis from optically active starting materials or by asymmetric synthesis. It will be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However when a specific term such as "butyl" is used, it is specific for the straight chain or "normal" butyl group, branched chain isomers such as "t-butyl" being referred to specifically when intended.

Preferably $R^1$ is hydrogen, amino, halogeno, cyano, (1–6C)alkyl or (1–6C)alkoxy.

Preferably $T^1$ is selected from N and CH. Preferably $T^3$ is selected from N and CH.

Preferably X is $SO_2$.

Particular values for optional substituents which may be present on Q include, for example,

| | |
|---|---|
| for alkyl; | (1–4C)alkyl, such as methyl, ethyl, propyl, isopropyl, butyl, isobutyl, sec-butyl or tert-butyl; |
| for cycloalkyl | cyclopropyl, cyclobutyl or cyclopentyl; |
| for cycloalkylalkyl | (3–6C)cycloalkyl(1–2C)alkyl such as cyclopropylmethyl, cyclopropylethyl, cyclobutylmethyl or cyclopentylmethyl; |
| for alkenyl; | (2–4C)alkenyl, such as allyl, prop-1-enyl, 2-methyl-2-propenyl or 2-butenyl; |
| for alkynyl; | (2–4C)alkynyl, such as prop-2-ynyl or but-2-ynyl; |
| for alkoxy; | (1–6C)alkoxy, such as methoxy, ethoxy, propoxy, isopropoxy, butoxy, pentoxy or 3-methylbutoxy; |
| for alkylamino; | (1–4C)alkylamino, such as methylamino, ethylamino, propylamino or butylamino; |
| for di-alkylamino; | di-[(1–4C)alkyl]amino such as dimethylamino, diethylamino, methylpropylamino or dipropylamino; |
| for alkylcarbamoyl; | (1–4C)alkylcarbamoyl such as N-methylcarbamoyl, N-ethylcarbamoyl, N-propylcarbamoyl, N-butylcarbamoyl or N-tert-butylcarbamoyl or N-(2-methylpropyl)carbamoyl; |
| for di-alkylcarbamoyl; | di-[(1–4C)alkyl]carbamoyl, N,N-dimethylcarbamoyl or N,N-diethylcarbamoyl; for |
| alkoxycarbonyl; | (1–4C)alkoxycarbamoyl such as methoxycarbonyl, ethoxycarbonyl, propoxycarbonyl, iso-propoxycarbonyl, butyoxycarbonyl or tert-butoxycarbonyl; |
| for alkylthio; | (1–4C)alkylthio such as methylthio ethylthio, propylthio, isopropylthio or butylthio; |
| for alkylsulphinyl; | (1–4C)alkylsulphinyl such as methylsulphinyl, ethylsulphinyl, propylsulphinyl, isopropylsulphinyl or butylsulphinyl; |
| for alkylsulphonyl; | (1–4C)alkylsulphonyl such as methylsulphonyl, ethylsulphonyl, propylsulphonyl,isopropylsulphonyl or butylsulphonyl; |
| for halogeno; | fluoro, chloro, bromo or iodo; |
| for halogenoalkyl; | halogeno(1–4C)alkyl such as halogenoalkyl containing one, two or three halo groups selected from fluoro, chloro, bromo and iodo and an alkyl group selected from methyl, ethyl,propyl, iso-propyl, butyl, iso-butyl and sec-butyl, thus particular values will include trifluoromethyl, difluoromethyl and fluoromethyl; |
| for alkanoylamino; | (1–4C)alkanoylamino such as formamido, acetamido. propionamido, isopropionamido, butyramido and iso butyramido; |
| for alkylenedioxy; | methylenedioxy or ethylenedioxy; |
| for alkanoyl; | (1–4C)alkanoyl such as formyl, acetyl, propionyl or butyryl; |

Particular values for Q when it is heteroaryl which comprises a 5- or 6-membered monocyclic heteroaryl ring containing up to 3 heteroatoms selected from the group consisting of oxygen, nitrogen and sulphur is, for example, furyl, thienyl, pyridyl, pyrazinyl, pyrimidinyl, pyridazinyl, pyrrolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including through any available nitrogen atom.

Particular values for optional substituents on the heterocyclic rings containing $T^1$ and $T^2$ include, for example,

| for alkyl; | (1–4C)alkyl such as methyl, ethyl, propyl, isopropyl, butyl, isobutyl, sec-butyl or tert-butyl; |
|---|---|
| for alkoxy; | (1–4C)alkoxy such as methoxy, ethoxy, propoxy, isopropoxy or butoxy; |
| for phenylalkyl; | phenyl (1–2C)alkyl such as benzyl, 2-phenylethyl or 1-phenylethyl |
| for halogeno; | fluoro, chloro, bromo or iodo |
| for alkoxycarbonyl; | methoxycarbonyl, ethoxycarbonyl, isopropoxycarbonyl or butyoxycarbonyl; |

A particular value for Q when it phenyl is 4-phenyl and when it is substituted phenyl is, for example 4-halophenyl such as 4-chlorophenyl or 4-bromophenyl.

A particular value for Q when it is naphthyl is 1-naphthyl or 2-naphthyl and when it is substituted naphthyl is 6-chloro or bromo naphth-1-yl or is 6-chloro or bromo naphth-2-yl.

A particular value for Q when it is phenylalkenyl is, for example, phenyl(2–C)alkenyl such as styryl, cinnamyl or 3-phenylprop-2-enyl.

In general, the heterocyclic rings containing $T^1$ and $T^2$ will be unsubstituted or bear one or two substituents selected from those hereinbefore defined.

In general, Q will be unsubstituted or will bear one, two or three (preferably one or two) substituents selected from these hereinbefore defined.

A preferred value for X is $SO_2$.

Specific values for optional substituents on the heterocyclic ring containing $T^1$ or the heterocyclic ring containing $T^2/T^3$ include, for example (1–6C)alkyl (such as methyl) and (1–6C)alkoxycarbonyl (such as methoxycarbonyl or ethoxycarbonyl).

Specific values for optional substituents for Q include, for example, halogeno (such as fluoro, chloro, bromo or iodo), (1–6C)alkoxy (such as methoxy or ethoxy), (1–6C)alkyl (such as methyl, iso-propyl or t-butyl), halogeno(1–6C)alkyl (such as trifluoromethyl), di-[(1–4C)alkyl]amino (such as dimethylamino), nitro, cyano, (1–6C)alkyl (such as methyl, ethyl, propyl or butyl), (1–6C)alkanoylamino (such as acetylamino) and pyridyl.

Specific values for a, b, c and d include, for example, a=2, b=2, c=2 and d=2; a=2, b=3, c=2 and d=2; a=2, b=2, c=2 and d=1.

Specific values for $R^1$ include, for example, hydrogen, amino, (1–6C)alkyl (such as methyl) and halogeno (such as chloro).

In a particular aspect the heterocyclic rings containing $T^1$ and $T^2$ are unsubstituted.

In each of the embodiments mentioned below particular, preferred and specific values include the appropriate values mentioned above, and wherein the heterocyclic ring containing $T^1$ and the heterocyclic ring containing $T^2$ may, independently, be optionally substituted by one or more substituents selected from (1–6C)alkyl, (1–6C)alkoxy, phenyl(1–4C)alkyl, halogeno and (1–6C)alkoxycarbonyl but preferably both are unsubstituted.

In one embodiment of the present invention, a, b, c and d are each 2, $T^1$ is CH, $T^2$ is N, Q is phenyl which bears one or two substituents independently selected from halogeno and (1–6C)alkyl, and X, $T^3$, $R^1$ and m are as hereinbefore defined.

In a further embodiment of the present invention, a, b, c and d are each 2, $T^1$ is CH, $T^2$ is N, Q is phenyl which bears one or two substituents independently selected from halogeno and (1–6C)alkyl, and X, $T^3$, $R^1$ and m are as hereinbefore defined.

In a further embodiment of the present invention, a, b, c and d are each 2, $T^1$ is N, $T^2$ is N, $T^3$ is N, Q is phenyl which bears one or two substituents independently selected from halogeno and (1–6C)alkyl, and X, $R^1$ and m are as hereinbefore defined.

In a further embodiment of the present invention, a, b, c and d are each 2, $R^1$ is (1–6C)alkyl, m is 1, $T^1$ is CH, $T^2$ is N, Q is phenyl which bears one or two substituents independently selected from halogeno and (1–6C)alkyl, and $T^3$ and X is hereinbefore defined.

In a further embodiment of the present invention, a, b, c and d are each 2, $R^1$ is (1–6C)alkyl, m is 1, $T^1$ is N, $T^2$ is N, Q is phenyl which bears one or two substituents independently selected from halogeno and (1–6C)alkyl and $T^3$ and X is hereinbefore defined.

In a further embodiment of the present invention, a, b, c and d are each 2, $R^1$ is (1–6C)alkyl, m is 1, $T^1$ is N, $T^2$ is N, $T^3$ is N, Q is phenyl which bears one or two substituents independently selected from halogeno and (1–6C)alkyl and X is hereinbefore defined.

In a further embodiment of the present invention, a, b, c and d are each 2, $R^1$ is methyl, m is 1, $T^1$ is CH, $T^2$ is N, Q is phenyl which bears one or two substituents independently selected from halogeno and (1–6C)alkyl and $T^3$ and X is hereinbefore defined.

In a further embodiment of the present invention, a, b, c and d are each 2, $R^1$ is methyl, m is 1, $T^1$ is CH, $T^2$ is N, $T^3$ is N, Q is phenyl which bears one or two substituents independently selected from halogeno and (1–6C)alkyl and X is hereinbefore defined.

In a further embodiment of the present invention, a, b, c and d are each 2, $R^1$ is methyl, m is 1, $T^1$ is N, $T^2$ is N, $T^3$ is N, Q is phenyl which bears one or two substituents independently selected from halogeno and (1–6C)alkyl and X is hereinbefore defined.

In one embodiment of the present invention, a, c and d are each 2 and b is 3, $T^1$ is CH, $T^2$ is N, Q is phenyl which bears one or two substituents independently selected from halogeno and (1–6C)alkyl, and $T^3$, $R^1$ and m are as hereinbefore defined.

In a further embodiment of the present invention, a, c and d are each 2 and b is 3, $T^1$ is N, $T^2$ is N, Q is phenyl which bears one or two substituents independently selected from halogeno and (1–6C)alkyl, and $T^3$, $R^1$ and m are as hereinbefore defined.

In a further embodiment of the present invention, a, c and d are each 2 and b is 3, $T^1$ is N, $T^2$ is N, $T^3$ is N, Q is phenyl which bears one or two substituents independently selected from halogeno and (1–6C)alkyl, and $R^1$ and m are as hereinbefore defined.

In a further embodiment of the present invention, a, c and d are each 2 and b is 3, $R^1$ is (1–6C)alkyl, m is 1, $T^1$ is CH, $T^2$ is N, Q is phenyl which bears one or two substituents independently selected from halogeno and (1–6C)alkyl and $T^3$ and X is hereinbefore defined.

In a further embodiment of the present invention, a, c and d are each 2 and b is 3, $R^1$ is (1–6C)alkyl, m is 1, $T^1$ is N, $T^2$ is N, Q is phenyl which bears one or two substituents independently selected from halogeno and (1–6C)alkyl and $T^3$ and X is hereinbefore defined.

In a further embodiment of the present invention, a, c and d are each 2 and b is 3, $R^1$ is (1–6C)alkyl, m is 1, $T^1$ is N, $T^2$ is N, $T^3$ is N, Q is phenyl which bears one or two substituents independently selected from halogeno and (1–6C)alkyl and X is hereinbefore defined.

In a further embodiment of the present invention, a, c and d are each 2 and b is 3, $R^1$ is methyl, m is 1. $T^1$ is CH, $T^2$ is N, Q is phenyl which bears one or two substituents independently selected from halogeno and (1–6C)alkyl and $T^3$ and X is hereinbefore defined.

In a further embodiment of the present invention, a, c and d are each 2 and b is 3, $R^1$ is methyl, m is 1, $T^1$ is N, $T^2$ is N, Q is phenyl which bears one or two substituents independentiy selected from halogeno and (1–6C)alkyl and $T^3$ and X is hereinbefore defined.

In a further embodiment of the present invention, a, c and d are each 2 and b is 3, $R^1$ is methyl, m is 1, $T^1$ is N, $T^2$ is N, $T^3$ is N, Q is phenyl which bears one or two substituents independently selected from halogeno and (1–6C)alkyl and X is hereinbefore defined.

In a further embodiment of the present invention, a, c and d are each 2 and b is 3, $R^1$ is halogeno, m is 1, $T^1$ is CH, $T^2$ is N, Q is phenyl which bears one or two substituents independently selected from halogeno and (1–6C)alkyl and $T^3$ and X is hereinbefore defined.

In a further embodiment of the present invention, a, c and d are each 2 and b is 3, $R^1$ is halogeno, m is 1, $T^1$ is N, $T^2$ is N, Q is phenyl which bears one or two substituents independently selected from halogeno and (1–6C)alkyl and $T^3$ and X is hereinbefore defined. In a further embodiment of the present invention, a, c and d are each 2 and b is 3, $R^1$ is halogeno, m is 1, $T^1$ is N, $T^2$ is N, $T^3$ is N, Q is phenyl which bears one or two substituents independently selected from halogeno and (1–6C)alkyl and X is hereinbefore defined.

Further embodiments of interest include those in which $R^1$, m, a, b, c, d. X and Q are as defined in any one of the preceeding paragraphs and $T^1$, $T^2$ and $T^3$ are:

(a) $T^1$ is N, $T^2$ is N and $T^3$ is N;
(b) $T^1$ is N, $T^2$ is N amd $T^3$ is CH;
(c) $T^1$ is N, $T^2$ is CH and $T^3$ is N; or
(d) $T^1$ is CH, $T^2$ is CH and $T^3$ is N.

Compounds of special interest include those described in the accompanying examples and their pharmaceutically acceptable salts and are hence provided as a further feature of the present invention.

The compounds of formula I and their pharmaceutically acceptable salts may be prepared by processes known to be applicable to the preparation of structurally related compounds. These procedures are illustrated by the following representative processes in which the various groups and radicals such as $R^1$, m, G, $T^1$, $T^2$, $T^3$, X and Q are as hereinbefore defined (unless stated otherwise), and are provided as a further feature of the present invention. In cases where the compounds contain a group such as an amino. hydroxy. or carboxy group, this group may be protected using a conventional protecting group which may be removed when desired by conventional means.

(a) For compounds of formula I wherein $T^3$ is N reacting an acid of formula II, or a reactive derivative thereof, with an amine of formula III.

A suitable reactive derivative of an acid of formula II is, for example, an acyl halide such as an acyl chloride formed by the reaction of the acid with an inorganic acid chloride such as thionyl chloride. Further suitable reactive derivatives include a mixed anhydride such as an anhydride formed by the reaction of the acid with a chloroformate such as isobutyl chloroformate; an active ester such as an ester formed by the reaction of the acid and a phenol such as pentafluorophenol, an ester such as pentafluorophenyl trifluoroacetate or an alcohol such as N-hydroxybenzotriazole or N-hydroxysuccinimide; an acylazide, for example an azide formed by the reaction of the acid and an azide as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium for example n-butyl-lithium, or a dialkylamino-lithium, for example lithium di-isopropylamide, or, for example, an organic amine base such as, for example, pyridine, 2,6-lutidine, collidine, 4-dimethylaminopyridine. triethylamine. morpholine or diazabicyclo[5.4.0]undec-7ene. The reaction is also preferably carried out in a suitable inert solvent or diluent, for example dichloro methane, chloroform, carbon tetrachloride, tetrahydrofuran, 1.2-dimethoxyethane, N N-dimethylformamide, N,N-dimethylacetamide. N-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl. ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) For compounds of formula I in which $T^2$ is N, reacting an amine of formula IV, with a compound of formula Z-X-Q in which Z is a displaceable group.

The reaction will, in general, be conveniently carried out in the presence of a suitable base. Suitable bases are those mentioned in (a) above.

A suitable value for the displaceable group Z is, for example, a halogeno or sulphonyloxy group, for example a fluoro, chloro, bromo, mesyloxy or 4-tolylsulphonyloxy group.

The reaction is conveniently performed in a suitable inert solvent or diluent as defined hereinbefore and at a temperature in the range, for example. 0° to 150° C., conveniently at or near ambient temperature.

(c) For compounds of formula I in which $T^1$ is N, reacting an amine of formula V with an acid of formula VIII, or a reactive derivative thereof.

The reaction will, in general, be carried out in the presence of a suitable base as mentioned in (a) above. Suitable reactive derivatives are also mentioned in (a) above.

The reaction is conveniently performed in a suitable inert solvent or diluent as defined hereinbefore and at a temperature in the range, for example 0° to 150° C., conveniently at or near ambient temperature.

(d) Reacting a compound of formula VI in which Z is a displaceable group with an amine of formula VII.

The reaction will, in general, be carried out in the presence of a suitable base as mentioned in (a) above.

Suitable values for Z are those mentioned in (b) above.

The reaction is conveniently carried out in a suitable inert solvent as mentioned in (a) above and at a temperature in the range, for example 0C to 150° C., conveniently in the range 15° C. to 100° C.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups are mentioned under (a) above. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid. the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example by reaction of said compound with the appropriate acid (which affords a physiologically acceptable anion), or with the appropriate base (which affords a physiologically acceptable cation), or by any other conventional salt formation procedure.

When an optically active form of a compound of the formula I is required, it may be obtained, for example, by carrying out one of the aforesaid procedures using an optically active starting material or by resolution of a racemic form of said compound using a conventional procedure.

Compounds of formula II may be prepared by reacting a compound of formula IX. where Y is an ester suitably ethoxycarbonyl, with a compound of formula VI in an analogous process as described in (d) above, and subsequent conversion of the ester to the acid by reduction with an alkali metal hydroxide, such as LiOH in a suitable solvent such as tetrahydrofuran, suitably at ambient temperature. Compounds of formula IX are commercially available.

Compounds of formula III, where $T^2$ is N. may be prepared by reacting a compound of formula Z—X—Q with an excess of compound of formula X, where $T^2$ is N, X is hydrogen and P is hydrogen, in an analogous method as described in (b).

Compounds of formula IV, where $T^3$ is N, may be prepared by reacting a compound of formula II with a compound of formula X, where $T^3$ is N and X is hydrogen and if $T^2$ is N then P is a protecting group or if $T^2$ is CH then P is hydrogen, in an analogous method as described in (a) above. Compounds of formula X are commercially available.

Compounds of formula IV, where $T^3$ is CH, may be prepared by reacting a compound of formula V with a compound of formula X, where $T^3$ is CH and X is $CO_2H$ and if $T^2$ is N then P is a protecting group or if $T^2$ is CH then P is hydrogen, in an analogous manner as described in method (c) above.

Compounds of formula V may be prepared by may be prepared by reacting a compound of formula VI with a compound of formula IX, where if $T^1$ is CH then Y is hydrogen and if $T^1$ is N then Y is a protecting group, in an analogous manner as described in method (d) above. Compounds of formula VI are commercially available.

Compounds of formula VI may be prepared by conversion of the corresponding 4-hydroxypyrimidine analogue, for example by reacting with trichlorophosphate. 4-hydroxypyrimidine analogues are commercially available.

As mentioned previously, the compounds of the formula I (and their pharmaceutically-acceptable salts) are inhibitors of the enzyme oxido-squalene cyclase. Thus, the compounds of the present invention are capable or inhibiting cholesterol biosynthesis and hence in lowering cholesterol levels in blood plasma.

The beneficial pharmacological properties of the compounds of the present invention may be demonstrated using one or more of the following techniques.

(a) In vitro test to measure inhibition of oxido-sgualene cyclase

This test measures the inhibition of microsomal oxido-squalene cyclase in vitro by compounds at set concentrations in the incubation medium.

Microsomes are prepared from rat liver according to methods known in the art, for example, the method described in published European Patent Application No. 324.421 and stored in liquid nitrogen prior to assay. Assay vials are kept at 37° C. throughout the incubation. The microsomes typically contain 15–20 mg of protein per ml of microsomes. For assay, 1 ml of microsomes are diluted by the addition of 722 µl of 50 mM phosphate buffer pH 7.4.

Phosphate buffered Tween® 80 (polyoxyethylene sorbitan monolaurate) is prepared by adding 0.1 g Tween 80 to 100 ml of 50 mM phosphate buffer.

A stock solution of oxido-squalene is made up as a solution in ethanol (0.65 mg. ml.$^{-1}$). 18µl of radio-labelled oxido-squalene (1 µCi.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a $10^{-4}$M stock solution. Dilutions are made from the stock to give $10^{-5}$M, $10^{-6}$M etc.

Phosphate buffered Tween® 80 (28 µl) is placed in 5 ml disposable plastic vials and 4 µl of the solution of the test compound is added and mixed well. An aliquot of the oxido-squalene mix (15 µl) is added and the vials pre-incubated for 10 minutes at 37° C. A portion of the microsomes (14.6 µl) are then added and incubated for a further 1 hour. The reaction is stopped by the addition of 315 µl of a mixture of 16% KOH in 20% ethanol.

The samples are then placed in a water bath at 80° C. for 2 hours to saponify. At the end of this process water (630 µl) is added followed by hexane (5 ml). The samples are tumble mixed for 5 minutes and then centrifuged. The hexane phase is removed and evaporated under nitrogen. The samples are then reconstituted in 300 µl of a 80:20 mixture of a acetonitrile:isopropyl alcohol. The samples are then chromatographed using a Hichrom 30DsS1 column with an isocratic elution using a 95:5 mixture of acetonitrile:isopropyl alcohol and a flow rate of 1 ml,min$^{-1}$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

By way of example, the compound described in Example 10c below gave an IC$_{50}$ of 81 nM.

(b) In vivo test to measure inhibition of oxido-sgualene cyclase

The test involves administration of the compound to rats on a reversed lighting regimen. Female rats (35–55 g) are housed in reverse lighting conditions (red light from 0200h–400h) for a period of about 2 weeks prior to test. Animals are allowed free access to chow and drinking water throughout this period. At test, animals should weigh 100–140 g. The rats are dosed orally with the compound (typically 10–50 mg/kg) formulated in a polyethylene glycol/hydroxypropylmethyl cellulose mix. After 1 hour the rats are given triturated sodium meyalonate (15 µCi/kg) intraperitoneally. Two hours after administration of the compound the rats are terminated and a piece of liver removed and weighed. The tissue is saponified at 80° C. for 2 hours in an ethanolic/potassium hydroxide solution (80% w/v aqueous KOH diluted 1:10 with ethanol). Water (2 ml) is added and the mixture extracted with iso-hexane (2×5 ml). The organic extracts are combined, evaporated to dryness under a stream of nitrogen and the residue is dissolved in a mixture of acetonitrile/iso-propanol (300 µl). An aliquot (200 µl) of this solution is loaded onto a HPLC column to separate the sterols. The radio-label content of each fraction is assessed using a radio chemical flow detector. Inhibitors of oxido-squalene cyclase are classed as those compounds which caused a build up of substrate and a concomitant disappearance of cholesterol and its precursors. ED$_{50}$ values are generated in the usual manner.

By way of example, the compound described in Example 10c below gave 72% inhibition of cholesterol biosynthesis when dosed at 5 mg/kg.

No overt toxicity was detected when compounds of the formula I were administered at several multiples of their minimum inhibitory dose or concentration.

When used in the treatment of diseases and medical conditions such as those mentioned above it is envisaged that a compound of formula I (or a pharmaceutically acceptable salt thereof) will be administered orally. intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

As inhibitors of oxido-squalene cyclase, the compounds of the present invention may also find utility as antifungal agents, and so the present invention also provides a method of inhibiting cholesterol biosynthesis in fungi. In particular the present invention provides a method of treating fungal infections which comprises administration to a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

Compounds of general formula I and intermediates for their preparation are described in published International Patent Application No. WO96/10022.

The invention will now be illustrated by the following non-limiting Examples in which, unless otherwise stated:

(i) evaporations were carried out by rotary evaporation in vacuo;

(ii) operations were carried out at room temperature, that is in the range 18–26° C.:

(iii) flash column chromatography or medium pressure liquid chromatography (MPLC) was performed on silica gel (Merck Kieselgel Art.9385, obtained from E Merck, Darnstadt, Germany);

(iv) yields are given for illustration only and are not necessarily the maximum attainable by diligent process development;

(v) proton NMR spectra were normally determined at 200 MHz using tetramethylsilane (TMS) as an internal standard, and are expressed as chemical shifts (delta values) obtained in DMSO-$d_6$ (unless stated otherwise) in parts per million relative to TMS using conventional abbreviations for designation of major peaks: s, singlet, m. multiplet; t, triplet; br, broad; d, doublet:

(vi) all end-products were characterised by microanalysis, NMR and/or mass spectroscopy; and (vii) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl: EtOAc=ethyl acetate, $Et_2O$=ether, MeCN=acetonitrile, MeOH=methanol, EtOH=ethanol, PriOH=2propanol, $H_2O$=water.

EXAMPLE 1

4-Chloro-2-methylpyrimidine (135 mg) was added to a solution of 1-(4-bromophenylsulphonyl)-4-(4-piperidylcarbonyl)piperazine (415 mg) in THF (15 ml) containing triethylamine (0.2 ml). The mixture was heated under reflux for 16 hours. After cooling, the THF was evaporated. The residue was treated with $H_2O$(20 ml) and the aqueous extracted with ethyl acetate (3×20 ml). The combined organic phases were washed with saturated brine (1×20 ml) dried and evaporated to give an oil which was purified by chromatography on silica gel. Elution with dichloromethane/methanol/0.88 $NH_3$ (96:3:1) gave an oil. Trituration with diethyl ether (10 ml) gave, as a colourless solid, 1-(4-bromophenylsulphonyl)-4-[1-(2-methylpyrimidyl)-4-piperidylcarbonyl]piperazine (152 mg), mp 200–202° C.; NMR: 1.39–1.48 (m, 2H), 1.55–1.69 (m, 2H), 2.30 (s, 3H), 2.80–3.00 (m, 7H), 3.45–3.67 (m, 4H), 4.32 (m, 2H), 6.57 (d, 1H), 7.65 (d, 2H), 7.83 (d, 2H), 8.03 (d, 1H); EI-MS m/z 508 (M+H).

The starting 4-chloro-2-methylpyrimidine was prepared by the method described in Ger. Offen. DE 3905364 (Chem. Abs., 114, 81871).

EXAMPLE 2

4-Chloropyrimidine hydrochloride (3.5 g) was added to a stirred suspension of 1-benzyl-4-[4-piperidylcarbonyl] piperazine (6.6 g), triethylamine (12.8 ml) and ethanol (120 ml). The mixture was heated under reflux for four hours and evaporated in vacuo to yield a treacle like substance. The residue was partitioned between ethyl acetate and water. The organic phase was washed with brine, dried ($Na_2SO_4$) and evaporated. The residue was absorbed onto alumina and purified using dry flash chromatography eluting with increasingly polar mixtures of dichloromethane and methanol (1:0 to 98:2). The material obtained was triturated with diethylether to give 1-(benzyl)-4-[1 -(4-pyrimidinyl)-4-piperidylcarbonyl]piperazine (3.8 g, 45% yield), mp 107–108.5° C.;

NMR ($CDCl_3$): 1.80 (m, 4H), 2.45 (m, 4H), 2.80 (m, 1H), 3.00 (m, 2H), 3.60 (m, 6H), 4.40 (m, 2H), 6.50 (d, 1H), 7.35 (m, 5H), 8.15 (d, 1H), 8.55 (s, 1H); microanalysis, found C, 68.7; H, 7.4; N 19.0%; $C_{21}H_{27}N_5O$ requires: C, 69.0; H, 7.45; N 19.2%.

EXAMPLE 3

A solution of 4-cyanophenylsulphonyl chloride (363 mg) in dichloromethane (10 ml) was added to a stirred mixture of 1-[1-(4-pyrimidinyl)-4-piperidylcarbonyl] piperazine (412.5 mg) and triethylamine (0.28 ml) in dichloromethane (15 ml) and the resultant mixture was stirred at ambient temperature for 2 hours. The mixture was partitioned between dichloromethane and water, and the organic phase washed with water, dried ($Na_2SO_4$) and evaporated. The residue was purified by column chromatography using 0.5% methanol in dichloromethane. Recrystallisation from ethyl acetate/hexane gave, as a solid 1-(4-cyanophenylsulphonyl)-4-[1-(4-pyrimidinyl)-4-piperidylcarbonyl] piperazine (280 mg), mp 180–181° C.;

NMR ($CDCl_3$): 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.9 (s, 4H), 8.2 (dd, 1H) and 8.6 (s, 1H).

The starting material was prepared as follows:

N-Benzylpiperazine (40.0 ml) was added in one portion to a solution of succinimido- 1-t-butoxycarbonylpiperidine-4-carboxylate (75.0 g) in dry dichloromethane (1600 ml). The solution was stirred at ambient temperature under an atmosphere of argon for 17 hours. The solution was washed with water (500 ml) and saturated brine (250 ml). The organic layer was dried ($Na_2SO_4$) and evaporated. The residual oil was purified by chromatography on alumina. elutin, with dichloromethane to give 1-benzyl-4-[1-(t-butoxycarbonyl)-4-piperildylcarbonyl]piperazine as an oil;

NMR ($CDCl_3$): 1.4–1.5 (9H, s), 1.6–1.85 (4H, m), 2.4–2.5 (4H, t), 2.5–2.65 (1H, m) 2.67–2.83 (2H, m), 3.45–3.7 (6H, m). 4.05–4.2 (2H, m) and 7.2–7.35 (5H, m); m/z 388 $(M+H)^+$.

A solution of 1-benzyl-4-[1-(t-butoxycarbonyl)-4-piperidylcarbonyl]piperazine (115.7 g) in dry dichloromethane (222 ml) was added dropwise over 45 minutes to trifluoroacetic acid (575 ml), maintaining the temperature below 25° C. under an atmosphere of argon. The solution was stirred at 23–25° C. for 1 hour. The solution was evaporated using a bath temperature of 30° C. The residual oil was poured, in portions, into saturated aqueous sodium carbonate solution (770 ml) while maintaining the temperature below 30° C. The aqueous mixture was extracted with dichloromethane (3×575 ml). The dichloromethane extracts were combined, dried ($Na_2SO_4$) and evaporated to give 1-benzyl-4-(4-piperidylcarbonyl)piperazine (56.2 g, 65% yield) as a colourless solid;

NMR (CDCl$_3$+DMSOd$_6$): 1.84–2.1 (4H, m), 2.33–2.5 (4H, m), 2.78–2.93 (1H,m), 2.93–3.12 (2H, m) 3.32–3.45 (2H, m), 3.45–3.65 (6H, m) and 7.2–7.37 (5H, m); m/z 288 (M+H).

Ammonium formate (1.88 g) was added to a mixture of 1-benzyl-4-[1-(4-pyrimidinyl)-4-piperidylcarbonyl] piperazine (2.73 g) and 10% palladium on carbon catalyst (0.55 g) in methanol (70 ml) under an atmosphere of argon. The mixture was stirred under reflux for 1 hour. The cooled mixture was filtered through diatomaceous earth and the filtercake was well washed with methanol. The filtrate and washings were combined and evaporated. The residual oil was suspended in saturated aqueous sodium carbonate solution (30 ml) and the mixture was extracted with dichloromethane (4×100 ml). The dichloromethane extracts were combined, dried (Na$_2$SO$_4$) and evaporated to give 1-[1-(4-pyrimidinyl)-4-piperidylcarbonyl]piperazine (1.94 g, 94%) as an off-white solid; NMR (CDCl$_3$): 1.75–1.95 (m, 4H), 2.7–3.15 (m, 8H), 3.4–3.7 (m, 4H), 4.3–4.47 (m, 2H), 6.45–6.55 (d, 1H), 8.12–8.23 (d, 1H) and 8.52–8.63 (s, 1H); m/z 276 (M+H).

EXAMPLE 4

Using an analogous procedure to that described in Example 7, 1-[1-(4-pyrimidinyl)-4-piperidylcarbonyl] piperazine was reacted with the appropriate sulphonyl chloride to give the compounds listed below in the table below

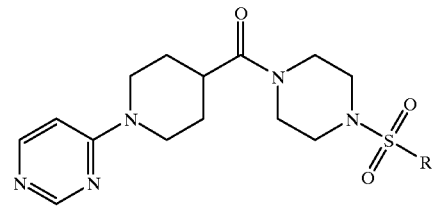

| Compound No. | R | mp (° C.) | NMR (CDCl$_3$) |
|---|---|---|---|
| 1 | 4-cyanophenyl | 180–181 | 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.9 (s, 4H), 8.2 (dd, 1H) and 8.6 (s, 1H). |
| 2 | 2-chloro 4 cyano phenyl | 137–138 | 1.7–1.8 (m, 4H), 2.7 (m, 1H), 2.9–3.0 (m, 2H), 3.2–3.5 (m, 4H), 3.6–3.8 (m, 4H), 4.4 (d, 2H), 6.5 (d, 1H), 7.7 (dd, 1H), 7.9 (s, 1H), 8.2 (dd, 1H), 8.2 (d, 1H) and 8.6 (s, 1H). |
| 3 | 3,4-dichloro phenyl | 189–190 | 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.5–7.7 (m, 2H), 7.9 (s 1H), 8.2 (dd, 1H) and 8.6 (s, 1H). |
| 4 | 4-methoxy phenyl | 205–206 | 1.7–1.8 (m, 4H), 2.7 (m, 1H), 2.9–3.0 (m, 2H), 3.0–3.1 (m, 4H), 3.6–3.8 (m, 4H), 3.9 (s, 3H), 4.4 (d, 2H), 6.5 (d, 1H), 7.0 (d, 2H), 7.7 (d, 2H), 8.2 (dd, 1H) and 8.6 (s, 1H). |
| 5 | 4-chlorophenyl | 196–197 | 1.7–1.8 (m, 4H), 2.7 (m, 1H), 2.9–3.0 (m, 6H), 3.6–3.8 (m, 4H), 4.4 (d, 2H), 6.5 (d, 1H), 7.5 (d, 2H), 7.7 (d, 2H), 8.2 (d, 1H) and 8.6 (s, 1H). |
| 6 | 2-cyanophenyl | sublimed 100 | 1.7–1.8 (m, 4H), 2.75 (m, 1H), 3.0 (m, 2H), 3.1–3.5 (m, 4H), 3.6–3.8 (m, 4H), 4.4 (d, 2H), 6.5 (d, 1H), 7.75 (m, 2H), 7.9 (dd, 1H), 8.15 (dd, 1H), 8.2 (d, 1H) and 8.55 (s, 1H). |
| 7 | 2,4-difluoro phenyl | decomp . . . 170–175 | 1.7–1.8 (m, 4H), 2.75 (m, 1H), 3.0 (m, 2H), 3.25 (m, 4H), 3.6–3.8 (m, 4H), 4.4 (d, 2H), 6.5 (d, 1H), 7.0 (m, 2H), 7.8 (m, 1H), 8.15 (d, 1H) and 8.55 (s, 1H). |
| 8 | 4-(n-butoxy) phenyl | 115–117 | 0.95–1.05 (t, 3H), 1.4–1.65 (m, 2H), 1.65–1.9 (m, 6H), 2.6–2.8 (m, 1H), 2.85–3.1 (m, 6H), 3.5–3.8 (m, 4H), 3.95–4.05 (t, 2H), 4.3–4.45 (m, 2H), 6.45–6.5 (dd, 1H), 6.95–7.05 (d, 2H), 7.6–7.7 (d, 2H), 8.15–8.2 (d, 1H), 8.55–8.6 (s, 1H). |
| 9 | 4-t-butylphenyl | 220–221 | 1.3–1.4 (s, 9H), 1.65–1.9 (m, 4H), 2.6–2.8 (m, 1H), 2.9–3.1 (m, 6H), 3.55–3.8 (m, 4H), 4.3–4.45 (m, 2H), 6.45–6.5 (dd, 1H), 7.5–7.6 (d, 2H), 7.6–7.7 (d, 2H), 8.15–8.2 (d, 1H), 8.55–8.6 (s, 1H). |
| 10 | 4-isopropyl phenyl | 170–171 | 1.2–1.35 (d, 6H), 1.65–1.9 (m, 4H), 2.6–2.8 (m, 1H), 2.85–3.15 (m, 6H), 3.55–3.8 (m, 4H), 4.3–4.45 (m, 2H), 6.45–6.55 (dd, 1H), 7.35–7.45 (d, 2H), 7.6–7.7 (d, 2H), 8.15–8.2 (d, 1H), 8.55–8.6 (s, 1H). |
| 11 | 3,5-dimethyl 4-fluorophenyl | 180–181 | 1.7–1.8 (m, 4H), 2.3 (s, 6H), 2.7 (m, 1H), 2.9–3.1 (m, 6H), 3.6–3.8 (m, 4H), 4.4 (m, 2H), 6.5 (dd, 1H), 7.4 (d, 2H), 8.2 (d, 1H), and 8.6 (s, 1H). |
| 12 | 2,5-dibromo 3,6-difluoro phenyl | 148–149 | 1.7–1.8 (m, 4H), 2.7 (m, 1H), 3.0 (m, 2H), 3.3–3.5 (m, 4H), 3.6–3.8 (m, 4H), 4.4 (d, 2H), 6.5 (d, 1H), 7.6 (m, 1H), 8.2 (d, 1H) and 8.6 (s, 1H). |

-continued

| Compound No. | R | mp (° C.) | NMR (CDCl$_3$) |
|---|---|---|---|
| 13 | 4-iodophenyl | 194–195 | 1.7–1.8 (m, 4H), 2.7 (m, 1H), 2.9–3.1 (m, 6H), 3.6–3.8 (m, 4H), 4.4 (d, 2H), 6.5 (d, 1H), 7.4 (d, 2H), 7.9 (d, 2H), 8.2 (d, 1H) and 8.6 (s, 1H). |
| 14 | 4-acetylamino phenyl | 273–275 | 1.7–1.8 (m, 4H), 2.2 (s, 3H), 2.7 (m, 1H), 2.9–3.1 (m, 6H), 3.6–3.8 (m, 4H), 4.4 (d, 2H), 6.5 (d, 1H), 7.5 (s, 1H), 7.7 (s, 4H), 8.2 (d, 1H) and 8.6 (s, 1H). |
| 15 | phenyl | 159–160 | 1.7–1.8 (m, 4H), 2.7 (m, 1H), 2.9–3.1 (m, 6H), 3.6–3.8 (m, 4H), 4.4 (d, 2H), 6.5 (d, 1H), 7.6 (m, 3H), 7.8 (dd, 2H), 8.2 (d, 1H) and 8.6 (s, 1H). |
| 16 | 4-ethylphenyl | 171–174 | 1.2–1.35 (t, 3H), 1.65–1.9 (m, 4H), 2.6–2.8 (m, 3H), 2.85–3.1 (m, 6H), 3.5–3.8 (m, 4H), 4.3–4.45 (m, 2H), 6.45–6.5 (d, 1H), 7.3–7.4 (d, 2H), 7.6–7.7 (d, 2H), 8.15–8.2 (d, 1H) and 8.55–8.6 (s, 1H). |
| 17 | 4-(n-propyl) phenyl | 138–140 | 0.87–1.03 (t, 3H), 1.6–1.9 (m, 6H), 2.55–2.8 (m, 3H), 2.85–3.15 (m, 6H), 3.55–3.8 (m, 4H), 4.3–4.5 (m, 2H), 6.45–6.55 (d, 1H), 7.3–7.4 (d, 2H), 7.6–7.7 (d, 2H), 8.15–8.25 (d, 1H) and 8.55–8.6 (s, 1H). |
| 18 | 2,2,2-trifluoroethyl phenyl | foam | $^1$H-NMR (200/250 mhz)(CDCl$_3$):δ:1.73–1.83 (m, 4H), 2.72–2.83 (m, 1H), 2.96–3.06 (m, 2H), 3.35–3.43 (m, 4H), 3.60–3.78 (m, 6H), 4.35–4.46 (m, 2H), 6.52 (dd, 1H), 8.20 (d, 1H), 8.60 (s, 1H). |
| 19 | 4-tolyl | 191–192 | 1.7–1.8 (m, 4H), 2.4 (s, 3H), 2.7 (m, 1H), 2.9–3.1 (m, 6H), 3.6–3.8 (m, 4H), 4.4 (d, 2H), 6.5 (d, 1H), 7.3 (d, 2H), 7.6 (d, 2H), 8.2 (d, 1H) and 8.6 (s, 1H). |
| 20 | 2,5-dibromo phenyl | 152–153 | 1.7–1.8 (m, 4H), 2.75 (m, 1H), 3.0 (m, 2H), 3.2–3.5 (m, 4H), 3.6–3.8 (m, 4H), 4.4 (d, 2H), 6.5 (d, 1H), 7.5 (dd, 1H), 7.6 (d, 1H), 8.2 (d, 1H), 8.25 (d, 1H) and 8.6 (s, 1H). |
| 21 | 3,5-bis-trifluoromethyl phenyl | 227–228 | 1.7–1.8 (m, 4H), 2.7 (m, 1H), 3.0 (m, 2H), 3.2 (m, 4H), 3.6–3.8 (m, 4H), 4.4 (d, 2H), 6.5 (d, 1H), 8.15 (d, 1H), 8.2 (m, 3H) and 8.6 (s, 1H). |
| 22 | 4-nitrophenyl | 219–220 | 1.7–1.8 (m, 4H), 2.7 (m, 1H), 2.9–3.0 (m, 2H), 3.1–3.2 (m, 4H), 3.6–3.8 (m, 4H), 4.4 (d, 2H), 6.5 (d, 1H), 8.0 (d, 2H), 8.2 (d, 1H), 8.4 (d, 2H) and 8.6 (s, 1H). |
| 23 | 4-chloro-3-nitrophenyl | 246–248 | 1.7–1.8 (m, 4H), 2.7 (m, 1H), 2.9–3.0 (m, 2H), 3.1–3.2 (m, 4H), 3.6–3.8 (m, 4H), 4.4 (d, 2H), 6.5 (d, 1H), 7.8 (d, 1H), 7.9 (d, 1H), 8.15 (d, 1H), 8.2 (d, 1H) and 8.6 (s, 1H). |
| 24 | 2-methoxy carbonylphenyl | 133–134 | 1.7–1.8 (m, 4H), 2.75 (m, 1H), 3.0 (m, 2H), 3.2–3.3 (m, 4H), 3.6–3.8 (m, 4H), 3.95 (s, 3H), 4.4 (d, 2H), 6.5 (d, 1H), 7.5 (dd, 1H), 7.6 (m, 2H), 7.8 (dd, 1H), 8.2 (d, 1H) and 8.6 (s, 1H). |
| 25 | 3,4-dibromo phenyl | 192–194 | 1.65–1.9 (m, 4H), 2.6–2.8 (m, 1H), 2.9–3.15 (m, 6H), 3.55-3.85 (m, 4H), 4.3–4.48 (m, 2H), 6.45–6.55 (dd, 1H), 7.48–7.57 (dd, 1H), 7.8–7.85 (d, 1H), 7.95–8.0 (d, 1H), 8.15–8.25 (d, 1H) and 8.55–8.6 (s, 1H). |
| 26 | 2,4,5-trichloro phenyl | 157–159 | 1.65–1.9 (m, 4H), 2.65–2.85 (m, 1H), 2.9–3.1 (m, 2H), 3.2–3.5 (m, 4H), 3.5–3.8 (m, 4H), 4.3–4.5 (m, 2H), 6.45–6.55 (d, 1H), 7.65 (s, 1H), 8.15 (s, 1H), 8.15–8.2 (d, 1H) and 8.55–8.6 (s, 1H). |
| 27 | 2,4,6-trimethyl phenyl | 141–142 | 1.7–1.8 (m, 4H), 2.3 (s, 3H), 2.6 (s, 6H), 2.7 (m, 1H), 2.9–3.0 (m, 2H), 3.1–3.3 (m, 4H), 3.6–3.7 (m, 4H), 4.4 (d, 2H), 6.5 (d, 1H), 7.0 (s, 2H), 8.2 (d, 1H) and 8.6 (s, 1H). |
| 28 | 3,5-dichloro phenyl | 186–187 | 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.6 (s, 3H), 8.2 (dd, 1H) and 8.6 (s, 1H). |
| 29 | 2-chloro-4-fluorophenyl | 135–137 | 1.7–1.9 (m, 4H), 2.7 (m, 1H), 2.9–3.1 (m, 2H), 3.2–3.4 (m, 4H), 3.6–3.8 (m, 4H), 4.4 (d, 2H), 6.5 (d, 1H), 7.1 (m, 1H), 7.3 (m, 1H), 8.1 (d, 1H), 8.2 (d, 1H) and 8.6 (s, 1H). |
| 30 | 4-trifluoro methoxyphenyl | 178–179 | 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.4 (d, 2H), 7.8 (d, 2H), 8.2 (dd, 1H) and 8.6 (s, 1H). |

-continued

| Compound No. | R | mp (° C.) | NMR (CDCl₃) |
|---|---|---|---|
| 31 | 2-chloro-4-trifluoromethyl phenyl | 152–153 | 1.7–1.9 (m, 4H), 2.7–2.8 (m, 1H), 2.9–3.1 (m, 2H), 3.2–3.5 (m, 4H), 3.6–3.8 (m, 4H), 4.4 (d, 2H), 6.5 (d, 1H), 7.7 (dd, 1H), 7.8 (s, 1H), 8.2 (m, 2H) and 8.6 (s, 1H). |

EXAMPLE 5

4-[1-(4-Pyrimidinyl)piperazin-4-ylcarbonyl]piperidine (412 mg) was dissolved in dichloromethane (16 ml), cooled in an ice bath, stirred and treated dropwise with a mixture of 4-chlorophenylsulphonyl chloride (338 mg) and triethylamine (0.3 ml) in dichloromethane (16 ml). The reaction mixture was allowed to reach room temperature and stirred for 18 h before treating with saturated NaHCO₃ solution. This mixture was extracted twice with dichloromethane. The combined organic extracts were washed twice with water and brine, dried over MgSO₄, filtered and evaporated under reduced pressure to a yellow solid. The solid thus obtained was chromatographed through a 10 g silica "bond elut" prepacked column, eluting with 1% methanol, 1% ammonium hydroxide and 98% dichloromethane to obtain 1-(4-chlorophenylsulphonyl)-4-[1-(4-pyrimidinyl)piperazin-4-ylcarbonyl]piperidine (178 mg; 26% yield based on the amine), as a white solid, mp 125–128° C.;

NMR (CDCl₃): 1.75–1.89 (m, 2H), 1.88–2.02 (m, 2H), 2.45–2.58 (m, 3H), 3.48–3.81 (m, 10H), 6.51 (dd, 1H), 7.52 (dd, 2H), 7.73 (dd, 2H), 8.25 (d, 1H), 8.64 (d, 1H).

EXAMPLE 6

4-[1-(4-Pyrimidinyl)piperazin-4-ylcarbonyl]piperidine (385 mg) in dichloromethane (20 ml) was stirred at room temperature as a solid suspension and treated dropwise with 4-bromophenylsulphonyl chloride (385 mg) and triethylamine (0.4 ml) in dichloromethane (15 ml). The resulting clear yellow solution was stirred at the same temperature for a further 20 h and treated with saturated NaHCO₃ solution (40 ml). The mixture was extracted twice with dichloromethane and the combined organic extracts washed twice each with water and brine dried over anhydrous MgSO₄, filtered and evaporated under reduced pressure to a yellow solid. The solid was chromatographed through a 10 g silica bond elut prepacked column, eluting with 1% methanol, 1% ammonium hydroxide and 98% dichloromethane to give 1-(4-bromophenylsulphonyl)-4-[1-(4-pyrimidinyl) piperazin-4-ylcarbonyl]piperidine (209 mg; 30% yield based on the amine), as a colourless solid, mp 171–174° C.;

NMR (CDCl₃): 1.74–1.88 (m, 2H), 1.86–2.03 (m, 2H), 2.45–2.58 (m, 3H), 3.49–3.82 (m, 10H), 6.49 (dd, 1H), 7.60–7.71 (m, 4H), 8.25 (d, 1H), 8.62 (d, 1H).

The starting material was prepared as follows:

1-(t-Butoxycarbonyl)-4-[1-(4-pyrimidinyl)piperazin-4-ylcarbonyl] piperidine (5.23g) was dissolved in dichloromethane (50 ml) and treated at room temperature with trifluoroacetic acid (30 ml). The resulting pale yellow solution was stirred at the same temperature for 18 h. After this period the reaction mixture was evaporated under reduced pressure to a brown oil which was subsequently azeotroped with toluene. The resulting oil was basified with 40% w/v NaOH solution, taken up in dichloromethane and filtered through celite. The filtrate was washed twice with brine, dried over anhydrous MgSO₄, filtered and evaporated under reduced pressure to obtain the amine, a brown foam, 1.545 g (40% yield based on the bloc derivative);

NMR (CDCl₃): 1.67–1.80 (m, 4H), 2.64–2.79 (m, 3H), 3.15–3.25 (m, 2H), 3.55–3.79 (m, 8H), 6.51 (dd, 1H), 8.26 (d, 1H), 8.63 (d, 1H).

A further sample of the amine was obtained by washing the celite again with 10%, methanol, 1% ammonium hydroxide and 89% dichloromethane. The dichloromethane solution was washed with brine ( 3 times), dried over anhydrous MgSO₄, filtered and evaporated down to a complex white foam. The foam was chromatographed through 60 υm silica, el. eluting with 10% methanol, 1% ammonium hydroxide and 89% dichloromethane to obtain a further 676 mg (18% based on the boc derivative) of the amine.

4-Pyrimidinyl piperazine (2.473 g: 15 mmol) was dissolved in DMF (35 ml) and treated at room temperature with 1-[1-(t-butoxycarbonyl)piperidin-4-ylcarbonyloxy]-2,5-dioxopyrrolidine (4.9 g; 15 mmol). The resulting clear solution was stirred at the same temperature for 65 h to give a pale yellow solid suspension. The reaction mixture was poured onto water (350 ml) and extracted four times with dichloromethane. The combined organic extracts were washed twice with water and brine, dried over anhydrous MgSO₄, filtered and evaporated under reduced pressure to obtain a crude oil. The oil was dried on a high vacuum pump to yield a colourless solid which was recrystallised with ethyl acetate/i-hexane to afford 1-(t-butoxycarbonyl)-4-[1-(4-pyrimidinyl)piperazin-4-ylcarbonyl]piperidine as clourless crystals (5.05 g; 90% yield based on 4-pyrimidyl piperazine), m.p. 159–163° C.;

NMR (CDCl₃): 1.44 (s, 9H), 1.54–1.85 (m.4H), 2.59–2.70 (m, 1H), 2.74–2.86 (m, 2H), 3.56–3.82 (m, 8H), 4.11–4.22 (m, 2H), 6.52 (dd.1H), 8.25 (d, 1H), 8.63 (d, 1H).

1-(Benzyl)-4-(4-chloropyrimidin-6-yl)piperazine (58.0 g) was dissolved, with some heating, in methanol (700 ml), treated with 10% Pd on activated carbon (11.6 g) and agitated and hydrogenated at atmospheric pressure for 8 h. The catalyst was removed by filtering through celite. The filtrate thus obtained was then evaporated under reduced pressure to a yellow-brown viscous gum which was chromatographed through 60 υm silica gel, eluting with 5% methanol, 1% ammonium hydroxide and 94% dichloromethane to obtain 4-(4-pyrimidinyl)piperazine, as a white solid, 25 g (76% yield based on prehydrogenation substrate);

NMR (t, 4H), 3.50 (t, 4H), 6.75 (dd, 1H), 8.14 (d, 1H), 8.45 (d, 1H).

A mixture of 4,6-dichloropyrimidine (29.5 g), N-benzylpiperazine (44.0 g) and DIPEA (44 ml) was suspended in p-xylene (400 ml) and heated at 138° C. under reflux. After 18 hours the reaction mixture was allowed to cool to room temperature and filtered. The filtrate was evaporated using high vacuum pump apparatus to obtain 1-(benzyl)-4-(4-chloropyrimidin-6-yl)piperazine a brown solid, 60.5 g (105% based on 4,6-dichloropyrimidine);

NMR (CDCl$_3$): 2.51 (t, 4H), 3.56 (s, 2H), 3.65 (t, 4H), 6.47 (s, 1H), 7.27–7.37 (m, 5H), 8.36(s, 1H).

EXAMPLE 7

1-(4-Bromophenylsulphonyl)-4-[1-(t-butoxycarbonyl)4-piperidylcarbonyl]homopiperazine (290 mg) was dissolved in dichloromethane (15 ml). Trifluoroacetic acid (3 ml) was added and the reaction stirred at room temperature for 1 hour. The solvent was removed in vacuo to give the crude trifluoroacetic acid salt of the deprotected piperidine. The crude salt was dissolved in ethanol (15 ml). Triethylamine (1 ml) and 4-chloropyrimidine hydrochloride (90 mg) were added. The reaction was heated under reflux for 2 hours, and solvent removed in vacuo. The residue was partitioned between dichloromethane (50 ml) and aqueous sodium bicarbonate solution (50 ml). Product extracted with dichloromethane (2×50 ml), dried (MgSO$_4$) and solvent removed in vacuo. The product was purified on a bond elute column (10 g) eluting with dichloromethane and [1% methanol, 1% ammonia, 98% dichloromethane] to give 1-(4-bromophenylsulphonyl)-4-[1-(4-pyrimidinyl)-4-piperidylcarbonyl]homopiperazine as a foam (152 mg);

NMR (250MHz): 1.40–1.95 (m, 6H), 2.85–3.1 (m, 3H), 3.25–3.80 (m, 8H), 4.35–4.55 (m, 2H), 6.90 (d, 1H), 7.78 (d, 1H), 7.82 (d, 1H), 7.85–7.95 (m, 2H), 8.20 (d, 1H), 8.53 (s, 1H).

The starting material was prepared as follows:

1-[1-(1-Butoxycarbonyl)-4-piperidylcarbonyloxy]2,5-dioxopyrrolidine (450 mg) and 1-(4-bromophenylsulphonyl)1,4-diazepine (440 mg) were reflux in dichloromethane (25 ml) for 3 hours. The reaction was stood at room temperature for 60 hours. Solvent removed in vacuo. The residue was partitioned between ethyl acetate (50 ml) and dilute citric acid (50 ml). The organic layer was washed with brine, dried (MgSO4) and the solvent removed in vacuo. The product was purified on a silica bond elute column (10 g) eluting with ethyl acetate/hexane (40:60) raising polarity gradually to (60:40). 1-(4-Bromophenylsulphonyl)-4-[1-(t-butoxycarbonyl)-4-piperidylcarbonyl]homopiperazine was obtained as a foam (620 mg);

NMR (250MHz): 1.30–1.85 (m, 6H), 1.40 (3, 9H), 2.63–2.87 (m, 3H), 3.20–3.68 (m, 8H), 3.85–3.98 (m, 2H), 7.67–7.77 (m, 2H), 7.77–7.87 (m, 2H).

4-Bromophenylsulphonyl chloride (1.50 g) in dicblomethane (50 ml) was added slowly to a solution of homopiperazine (3.0 g) in dichloromethane (100 ml). The reaction was stirred at room temperature for 18 hours. The reaction mixture was washed with water (40 ml) and brine (150 ml), dried (MgSO4) and solvent removed in vacuo. The product was recrystallised from dichloromethane/hexane to give 1-(4-bromophenylsulphonyl) 1,4-diazepine a white solid (650 mg, mp 95–97° C.;

NMR (250MHz): 1.57–1.75 (m, 2H), 2.67–2.79 (m, 4H), 3.15–3.30 (m, 4H), 7.73 (d, 2H), 7.82 (d, 2H).

EXAMPLE 8

The lithium salt of 1-(4-pyrimidinyl)piperidine-4-carboxylic acid (426 mg), thionyl chloride (15 ml) and DMF (5 drops) were heated under reflux for 1.5 hours. The thionyl chloride was removed in vacuo. Toluene (20 ml) was added, and removed in vacuo to give the crude acid chloride. A solution of the 1-(4-bromophenylsulphonyl)piperazine (610 mg) and triethylamine (2 ml) in dichloromethane (10 ml) was added to a solution of the crude acid chloride in dichloromethane (5 ml), cooled in an ice bath. After addition of the reagents the ice bath was removed and the reaction was stirred at room temperature for 1 hour. Water (30 ml) was added. The mixture was washed with water (2×30 ml), dried (MgSO$_4$) and the solvent removed. The reaction mixture was purified on a silica bond elute column (10 g), eluting initially with dichloromethane and increasing polarity to 3% methanol, 1% ammonia, 96% dichloromethane. This gave 1-(4-bromophenylsulphonyl)-4-[1-(5-chloropyrimidin-4-yl)-4-piperidylcarbonyl]piperazine (280 mg) and the mono-chloro derivative (110 mg) as a foam, mp 165–167° C.

NMR (250MHz): 1.45–1.73 (m, 4H), 2.83–3.10 (m, 7H), 3.45–3.70 (m, 4H) 4.22–4.35 (m, 2H), 7.67 (d, 2H), 7.97 (d, 2H), 8.34 (s, 1H), 8.50 (s, 1H).

The starting material was prepared as follows:

A solution of 1-(4-pyrimidinyl)-4-(ethoxycarbonyl) piperidine (1.52 g) and lithium hydroxide monohydrate (300 mg) in ethanol (20 ml) and water (20 ml) were heated under reflux for 1.5 hours. The solvents were removed in vacuo to give the crude lithium salt of 1-(4-pyrimidinyl)piperidine-4-carboxylic acid (1.46 g) which was used without purification.

A solution of 4,6-dichloropyrimidine (5.22 g), ethyl isonipecotate (5.50 g) and triethylamine (7 ml) in ethanol (60 ml) was stirred at room temperature for 2 hours, and solvent removed in vacuo. The crude mixture partitioned between ethyl acetate (100 ml) and water (50 ml), washed with brine, dried (MgSO$_4$) and solvent removed to give 1-(6-chloropyrimidin-4-yl)-4-(ethoxycarbonyl)piperidine.

Ammonium formate (10 g) and 30% palladium on carbon (600 mg) was added to a solution of the crude mono-chloro pyrimidyl-piperazine in ethanol (70 ml). The reaction was stirred at room temperature for 18 hours and filtered through celite and the solvent removed in vacuo. Crude product was partitioned between dichloromethane/sodium bicarbonate solution and extracted with dichloromethane (3×50 ml). Combined extracts were dried (MgSO$_4$) and the solvent removed. The product was purified by flash column chromatography (3% methanol/ethyl acetate) to give 1-(4-pyrimidinyl)-4-(ethoxycarbonyl)piperidine an oil (5.44 g);

NMR (250MHz): 1.2 (t, 3H), 1.40–1.60 (m, 2H), 2.10–2.25 (m, 1H), 3.0–3.13 (m, 2H), 4.07 (q, 2H), 4.20–4.35 (m, 2H), 6.82 (d, 1H), 8.13 (d, 1H), 8.45 (s, 1H).

EXAMPLE 9

4-(1-(4-Bromophenylsulphonyl)piperazin-4-ylcarbonyl) piperidine (170 mg) and 4-chloropyrimidine.2 HCl in absolute alcohol (10 ml) and triethylamine (0.5 ml) were heated under reflux for two hours. The solution was evaporated in vacuo and water (50 ml) added and organic material was extracted into ethyl acetate (2×50 ml), washed with water, brine and dried (MgSO$_4$). The solution was evaporated in vacuo to give an oil which was dissolved in ethyl acetate and purified by flash chromatography on alumina (ICN Alumina N 32-63) using an increasing concentration of methanol in ethyl acetate (0–10%) as eluant. This gave a solid which recrystallised once from a mixture of ethyl acetate/tetrahydrofuran/isohexane and then from acetonitrile 1-(4-pyrimidinyl)-4-[1-(4-bromophenylsulphonyl)piperazin-4-ylcarbonyl]piperidine (1 55 mg), as a solid, m.p. 197–198° C.;

NMR: 1.7–1.9 (m, 4H), 2.6–2.8 (m, 1H), 2.9–0.2 (m, 6H), 3.5–3.8 (bs, 4H), 4.3–4.5 (dt, 2H), 6.45–6.55 (dd, 1H), 7.6–7.7 (d, 2H), 7.7–7.8 (d, 2H), 8.15–8.25 (d, 1H), 8.6, (s, 1 H); microanalysis, found: C, 48.2; H, 4.9; N, 13.9%;

$C_{20}H_{24}BrN_5O_3S$ requires: C, 48.6; H, 4.9; N,14.2%; MS m/z 494 (MH)⁺.

The starting material for was prepared as follows:

1-[1-(t-Butoxycarbonyl)-4-piperidylcarbonyloxy]-2,5-dioxo pyrrolidine (2.45 g) and 1-(4-bromophenylsulphonyl) piperazine (2.31 g) were stirred together in dichloromethane (100 ml) overnight. The solution was then stirred with water (100 ml) for 30 min, washed with further water, brine and dried (MgSO₄). The solution was evaporated in vacuo to give an oil which crystallised on standing to give 1-[1-(t-butoxycarbonyl)-4-piperidylcarbonylj-4-(1-(4-bromophenylsulphonyl)piperazine (3.64 g) mp 209–210° C.;

NMR: 1.45 (s, 9H), 1.49–1.81 (m, 4H), 2.51 (m, H), 2.72 (dt, 2H), 3.03 (t, 4H), 3.64 (bs, 4H), 4.11 (d.2H), 7.59 (d, 2H), 7.69 (d, 2H); MS m/z 515 (MH)⁺.

1-L 1-(t-Butoxycarbonyl)-4-piperidylcarbonyl]-4-(4-bromophenylsulphonyl)piperazine (3.3 g) was stirred in trifluoroacetic acid (20 ml) for one hour. The solvent was evaporated in vacuo and the residual oil was treated with ice and the solution basified by addition of solid potassium carbonate The organic material was extracted into ethyl acetate and washed with water and brine, dried (MgSO₄) and evaporated in vacuo to give 1-(4-bromophenylsulphonyl)-1-(4-piperidylcarbonyl)piperazine as an oil (2. Ig):

NMR: 1.52–1.79 (m, 4H), 2.43–2.71 (m, 3H), 3.01 (t, 4H) 3.13 (dt, 2H), 3.64 (s, 4H), 7.61 (d, 2H), 7.7 (d, 2H); MS m/z 415 (MH)⁺.

EXAMPLE 10

Using an analogous procedure to that described in Example 14; the following compounds were prepared.

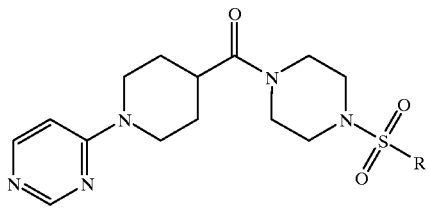

| Compound No. | Structure R = | mpt (° C.) | NMR |
|---|---|---|---|
| 1 | 4-methyl phenyl | 186–187 | (CDCl₃): 1.72–1.78(m, 4H), 2.45(s, 3H), 2.65–2.76(m, 1H), 2.89–3.09(m, 6H), 3.60–3.76(m, 4H), 4.33–4.44(m, 2H), 6.50(dd, 1H, 6.3, 1Hz), 7.35(d, 1H, 8.3Hz), 7.64 (d, 1H, 8.3Hz), 8.19 (d, 1H, 6.3Hz), 8.58(s, 1H). |
| 2 | 4-fluoro phenyl | 189–191 | 1.71–1.78(m, 4H), 2.70–2.74 (m, 1H), 2.93–3.09(m, 6H), 3.59–3.75(m, 4H), 4.33–4.43(m, 2H), 6.49(dd, 1H, 6.3, 1Hz), 7.23–7.27(m, 2H), 7.75–7.82(m, 2H), 8.18(d, 1H, 6.3Hz), 8.57(s, 1H). |

EXAMPLE 11

A solution of 4-cyanobenzoyl chloride (298 mg) in dichloromethane (10 ml) was added to a stirred mixture of 1-[1 (4-pyrimidinyl) piperidin-4-ylcarbonyl] piperazine (412.5 mg) and triethylamine (0.28 ml) in dichloromethane (15 ml) and the resultant mixture was stirred at ambient temperature for 2 hours. The mixture was partitioned between dichloromethane and water. The organic phase was washed with water, dried (Na₂SO₄) and evaporated. The residue was purified by column chromatography using 0.5 % methanol in dichloromethane. Recrystallisation from ethyl acetate/hexane gave, as a solid 1-(4-cyanobenzoyl)-4-[1-(4-pyrimidinyl)-4-piperidylcarbonyl]piperazine (280 mg), mp 192–193° C.;

NMR (CDCl₃): 1.8–1.9 (m, 4H), 2.8 (m, 1H), 2.9–3.0 (m, 2H), 3.4–3.9 (m, 8H), 4.4 (d, 2H), 6.5 (d, 1H), 7.5 (d, 2H), 7.8 (d, 2H), 8.2 (dd, 1H), 8.6 (s, 1H).

EXAMPLE 12

Using an analogous procedure to that described in Example 30; the following compounds were prepared.

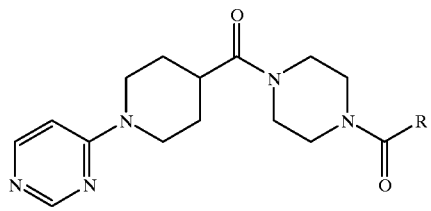

| Compound No | Structure R = | mpt (° C.) | NMR (CDCl₃) |
|---|---|---|---|
| 1 | 4-bromophenyl | 142–145 | 1.7–1.95(m, 4H), 2.7–2.9(m, 1H), 2.9–3.1(m, 2H), 3.4–3.85(m, 8H), 4.3–4.5(m, 2H), 6.5–6.55(dd, 1H), 7.25–7.35(d, 2H), 7.55–7.65(d, 2H), 8.15–8.2(d, 1H) and 8.6(s, 1H). |
| 2 | 4-fluorophenyl | 152–154 | 1.8–2.0(m, 4H), 2.7–2.9(m, 1H), 2.9–3.1(m, 2H), 3.4–3.9(m, 8H), 4.35–4.5(m, 2H), 6.5–6.55(d, 1H), 7.1–7.2(d, 2H), 7.4–7.5(d, 2H), 8.2–8.25(d, 1H) and 8.6(s, 1H). |
| 3 | 4-chlorophenyl | 132–135 | 1.65–1.95(m, 4H), 2.7–2.9(m, 1H), 2.95–3.1(m, 2H), 3.4–3.85(m, 8H), 4.35–4.5(m, 2H), 6.5–6.55(d, 1H), 7.32–7.48(m, 4H), 8.15–8.25(m, 1H) and 8.55–8.65(s, 1H). |

EXAMPLE 13

4-Bromophenylsulphonyl chloride (129 mg) was added at ambient temperature to a stirred solution of 1-[1-(4-pyrimidinyl)pyrrolidin-3-ylcarbonyl]piperazine (130 mg) in THF (8 ml) containing triethylamine (0.14 ml). The mixture was stirred for 2 hours then evaporated. The residue was treated with water (16 ml) and dichloromethane (30 ml) added. Aqueous was separated and re-extracted with dichloromethane (20 ml). The combined organic phases were washed with saturated brine (2×10 ml), dried and evaporated. The residue was purified by chromatography on neutral alumina eluting with dichloromethane/methanol (99/1 v/v) to give, as a colourless solid, 1-(4-bromophenylsulphonyl)-4-[1-(4-pyrimidinyl)pyrollidin-3-ylcarbonyl]piperazine (134 mg), mp 94–6°;

NMR (CDCl3) 2.05–2.42 (m, 2H), 2.90–3.17 (m, 4H), 3.20–3.40 (m, 1H), 3.35–3,55 (m, 1H), 3.55–3.90 (m, 7H), 6.26 (dd, 1H), 7.61 (d, 2H), 7.70 (d, 2H), 8.17 (d, 1H), 8.56 (s, 1H), EI-MS m/z480 (M+H).

The starting piperazine derivative used as starting material was prepared as follows:

Benzylchloroformate (2.86 ml) was added to a stirred suspension of N-benzyl-3-n-butoxy carbonyl pyrrolidine (1.75 g) and sodium bicarbonate (2.52 g) in dichloromethane (30 ml). The reaction was stirred for 0.5 hours, filtered and the filtrate evaporated to give an oil. The residual oil was purified by chromatography on silica gel; elution with ethyl acetate/hexane (1/9 v/v) gave, as a pale yellow oil, N-Cbz-3-n-butoxycarbonyl pyrrolidine (1.40 g);

NMR (CDCl3) 0.93 (t, 3H), 1.27–1.47 (m, 2H), 1.52–1.67 (m, 2H), 2.06–2.22 (m, 2H), 2.95–3.10 (m, 1H), 3.33–3.75 (m, 4H), 4.07 (t, 2H), 5.12 (s, 2H), 7.25–7.40 (m, 5H), E1-MS m/z 306 (M+H).

Aqueous 1M NaOH (6 ml) was added to a stirred solution of the above ester (1.37 g) in methanol (6 ml). After 1 hour, the methanol was evaporated. Water (20 ml) was added to the residue and 1M HCl (6 ml) was added dropwise to the stirred mixture. This aqueous phase was extracted with ethyl acetate (3×25 ml). The combined organic phases were washed with saturated brine (1×20 ml) dried and evaporated to give, as a colourless oil, N-Cbz-3-carboxy pyrrolidine (780 mg);

NMR (CDCl3) 2.1–2.25 (m, 2H), 3.00–3.15 (m, 1H), 3.32–3.74 (m, 4H), 5.10 (s, 2H) 7.17–7.38 (m, 5H); E1-MS m.z 248 (M-H).

N-t-Butoxycarbonyl piperazine (543 mg) was added to a solution of the above acid (727 mg) N-hydroxy benzotriazole (590 mg) in DMF (12 ml). 1-(3-Dimethylaminopropyl)-3 -ethyl carbodiimide hydrochloride (612 mg) was added and the mixture stirred for 16 hours.

The DMF was evaporated, water (50 ml) was added and the aqueous phase was extracted with ethyl acetate (3×25 ml). The combined organic phases were washed with saturated sodium bicarbonate solution (2×20 ml). The organic phase was dried and evaporated to give, as a creamy solid, 1-t-butoxy carbonyl-4-(1-Cbz-pyrrolidin-3yl carbonyl) piperazine (1.15 g): m.p. 70–74° C.;

NMR (CDCl3) 1.45 (s, 9H), 1.96–2.30 (m. 2H), 3.08–3.25 (m, 1H), 3.35–3.50 (m, 8H), 3.77 (m, 4H), 5.12 (s, 2H), 7.22–7.35 (m, 5H); El-MS m/z 418 (M+H).

10% palladium on carbon (75 mg) was added to a stirred solution of the above Cbz-pyrrolidinyl derivative (1.11 g) in ethanol (40 ml) and the mixture hydrogenated at 1 atmosphere H2 pressure 25° C. for 16 hours. The catalyst was removed by filtration through elite. The filtrate was evaporated to dryness to give a solid which was triturated with diethyl ether (10 ml). Filtration gave, as a colourless solid, 1-t-butoxycarbonyl-4-(1(H)pyrrolidin-3-yl carbonyl) piperazine (470 mg); mp 94–95° C.:

NMR (CDCl3) 1.48 (s, 9H), 1.88–2.08 (m. 2H), 2.78–3.25 (m, 5H), 3.46–3.62 (m, 2H), E1-MS m/z 284 (M+H).

4-Chloropyrimidine hydrochloride (210 mg) was added to a solution of the above Boc-piperazino derivative (380 mg) in ethanol (10 ml) containing triethylamine (0.6 ml). The mixture was stirred at reflux temperature for 16 hours. After cooling, the ethanol was evaporated. The residue was treated with saturated sodium bicarbonate solution (20 ml) and the aqueous extracted with ethyl acetate (3×20 ml). The combined organic phases were washed with saturated brine (2×20 ml), dried and evaporated. The residue was crystallised from ethyl acetate to give, as a pale grey solid, 1-t-butoxycarbonyl-4-[1-(4-pyrimidinyl)pyrroldin-3-yl carbonyl]piperazine (301 mg); mp 156–7° C., NMR 1.42 (s, 9H), 1.95–2.25 (m, 2H), 3.25–3.70 (m, 13H), 6.48 (dd, 1H) 8.12 (d, 1H), 8.43 (s, 1H): E1-MS m/z 362 (M+H).

Trifluoroacetic acid (TFA) (0.7 ml) was added to a stirred solution of the above pyrimidinyl-pyrrolidin carbonyl piperazine derivative (261 mg) in dichloromethane (5 ml) at 25°. After 1 hour, TFA (0.3 ml) was added. After a further 1 hour the dichloromethane/TFA mixture was evaporated. The residue was treated with saturated brine solution (2 ml) and 5M sodium hydroxide (2 ml). The aqueous phase was extracted with dichloromethane (5×15 ml). The combined organic phases were washed with saturated brine (2×25 ml), dried and evaporated to give, as a colourless solid, 4-[1-(4-pyrimidyl)pyrrolidin-3-ylcarbonyl]piperrazine (143 mg): m.p. 129–131° C.:

NMR (DMSOd6/CD3COOD) 1.95–2.25 (m, 4H), 2.97–3.20 (m, 4H), 3.30–3.85 (m, 9H), 6.45 (d, 1H), 8.09 (d, 1H), 8.45 (s, 1H); E1-MS m/z 262 (M+H).

EXAMPLE 14

2-Methyl-4-chloro-pyrimidine (0.34 g) was added to a suspension of 1-(4-bromophenylsulphonyl)-4-(1-piperazinylcarbonyl)piperidine (1.0 g) in ethanol (10 ml) and 1( triethylamine (0.5 ml). The reaction was heated under reflux for 2 hours, cooled and the solvent removed by evaporation. The reaction mixture was purified by filtration column chromatography (silica, gradient elution dichloromethane to 10% methanol in dichloromethane) to give 1-(4-bromophenylsulphonyl)-4-[1-(2-methylpyrimidin-4-yl)piperazin-4-ylcarbonyl]piperidine as a solid (0.82 g) mpt 239–240° C.; NMR (CDCl$_3$) 1.75–2.0 (m, 5H), 2.5 (m, 2H), 3.45–3.8 (m, 10H), 6.3 (m, 1H), 7.65 (m, 4H), 8.2 (m, 1H).

The starting material was prepared as follows.

A solution of 4-bromophenylsulphonyl chloride (7.68 g) in dichloromethane (100 ml) was added dropwise over a period of 30 minutes to a solution of 4-(ethoxycarbonyl) piperidine (4.71 g) in dichloromethane (50 ml) at 0° C. and under argon. The mixture was stirred overnight during which time it was allowed to warm to room temperature. The organic phase was washed with water, brine, dried and evaporated to give a solid. This solid was triturated in petroleum ether (bp 40–60° C.) to give 1-(4-bromophenylsulphonyl)-4-(ethoxycarbonyl)piperidine (10.05 g), m.p. 137–133° C.

An aqueous 40% (w/v) sodium hydroxide solution (10 ml) was added to a stirred mixture of 1-(4-bromophenylsulphonyl)-4-(ethoxycarbonyl)piperidine (8.0 g) and ethanol (100 ml) at 25° C. A precipitate was formed. Water (100 ml) was added and the mixture stirred for a further 2 hours. The mixture was evaporated to dryness and the residue was dissolved in hot water (95° C., 470 ml). The solution was allowed to cool overnight. The solid was collected by filtration and suspended in water (125 ml). Acetic acid (1.4 ml) was added slowly to give pH6 and the solid was collected by filtration. There was thus obtained 1-(4-bromophenylsulphonyl)-4-carboxypiperidine (5.66 g), m.p. 224–7° C.

N-Hydroxybenzotriazole (2.02 g) was added to a stirred solution of 1-(4-bromophenylsulphonyl)-4-carboxypiperidine (3.48 g) in DMF (40 ml) at 20° C. under argon. After 10 minutes, N-(t-butoxycarbonyl)piperazine (1.86 g) was added followed by 1-(3-dimethylaminopropyl)-3-ethylcarbodiimide (2.09 g). The mixture was stirred overnight under argon. The DMF was removed by evaporation. Water (150 ml) was added to the residue to give a solid which was collected by filtration and washed with water.

There was thus obtained 1-(4-bromophenylsulphonyl)-4-[1-(t-butoxycarbonyl)piperazin-4-ylcarbonyl]piperidine which was recrystallised from propan-2-ol to give a solid (3.53 g), m.p. 201–4° C.

1-(4-bromophenylsulphonyl)-4-[1-(t-butoxycarbonyl)-4-piperidylcarbonyl]piperidine (3.42 g) was added to trifluoroacetic acid (22 ml) at 0° C. under argon. The mixture was stirred for 1 hour at a temperature between 0 and 10° C. The excess trifluoroacetic acid was removed by evaporation. Ice (50 g) was added to the residue, followed by a saturated aqueous potassium carbonate solution (10 ml). The mixture was extracted with dichloromethane (3×100 ml). The extracts were combined, washed with brine, dried ($Na_2SO_4$) and evaporated to give 1-(4-bromophenylsulphonyl)-4-(1-piperazinylcarbonyl)piperidine as a solid (2.64 g), m.p. (8–9° C. NMR ($CDCl_3$): 1.55–1.97 (m, 4H), 2.35–2.62 (m, 3H), 2.70–2,85 (t, 4H), 3.27–3.62 (bd, 4H), 3.68–3.80 (dt, 2H), 7.52–7.70 (m, 4H).

EXAMPLE 15

Thionyl chloride (5 ml) was added to the lithium salt of 1-(4-pyrimidinyl)piperidine 4-carboxylic acid (320 mg). DMF (2 drops) was added and the reaction was stirred at room temperature for 1 hour. The reaction mixture was evaporated in vacuo. Toluene (10 ml) was added and then removed by evaporation to give the crude acid chloride. The residue was dissolved in dichloromethane (15 ml), to which was added triethylamine (1.5 ml) and 1-(4-chlorophenylsulphonyl)homopiperazine (412 mg). The reaction was stirred at room temperature for 1 hour. The reaction was washed with water, dried (MgSO4) and solvent removed by evaporation.

Purification by chromatography (bond elut, silica; gradient elution, dichloromethane to 1% methanol, 1% ammonia in dichloromethane) gave 1-(4-chlorophenylsulphonyl)-4-[1-(4-pyrimidinyl)-4-piperidylcarbonyl]homopiperazine as a foam (326 mg); NMR ($DMSOd_6$): 1.45–2.0 (m, 6H), 2.90–3.15 (m, 3H), 3.3–3.8 (m, 8H), 4.40–4.05 (m, 2H), 6.95 (dd, 1H), 7.80 (m, 2H), 7.90 (m, 2H), 8.25 (d, 1H), 8.58 (s, 1H).

The 1-(4-chlorophenylsulphonyl)homopiperazine was prepared as follows. 4-Chlorophenylsulphonyl chloride (3.74 g) in dichloromethane (100 ml) was added slowly to a solution of homopiperazine (6.73 g) in dichloromethane (100 ml). The reaction was stood at room temperature overnight. The reaction was washed with water, dried (MgSO4) and the solvent removed in vacuo. The residue was triturated with 20% ether in hexane to give 1-(4-chlorophenylsulphonyl)homopiperazine (3.71 g); NMR ($DMSOd_6$): 1.65 (m, 2H), 2.73 (m, 4H), 3.2–3.65 (m 4H), 7.7 (m, 2H), 7.8 (m, 2H).

EXAMPLE 16

1-(4-trifluoromethylphenylsulphonyl)homopiperazine (1.85 g) in 20 ml dichloromethane and 4 ml triethylamine was treated with a solution of 1-(2-methylpyrimidin-4-yl)-4-(acylchloride)piperidine (prepared from 2 g acid and thionyl chloride ) in 20 ml dichloromethane After overnight stirring the reaction mixture was washed with water, followed by saturated sodium bicarbonate solution and brine. Dried over magnesium sulphate, evaporated and chromatographed (Bondelut 10 g, dichloromethane followed by 1% methanol/dichloromethane/1% ammonia) to give 1-(4-trifluoromethylphenylsulphonyl)- 1-[1-(2-methylpyrimidin-4-yl)-4-piperidylcarbonyl)homopiperazine (2.0 g) as a colourless foam;

NMR ($CDCl_3$): 1.65–1.95 (4H,m), 1.95–2.1 (2H,m), 2.5 (3H,S), 2.66–2.77 (1H,m), 2.88–3.0 (2H,m), 3.28–3.4 (3H, m), 3.4–3.5 (1H,m), 3.63–3.78 (4H,m), 4.25 (2H,d), 7.78–7.84 (2H,m), 7.9–7.97 (2H,m), 8.1 (1H,d) .

The 1-(4-trifluoromethylphenylsulphonyl) homopiperazine was prepared as follows. 4-Trifluoromethylphenylsulphonylchloride (1.5 g) in 20 ml dichloromethane was added dropwise to 5 g homopiperazine and 1.8 ml triethylamine in 55 ml dichloromethane and left stirring overnight. Washed with water and brine, dried ($MgSO_4$), and evaporated to give 1-(4-trifluoromethylphenylsulphonyl)homopiperazine (1.80 g) as a colourless solid; NMR ($CDCl_3$) 1.75 (1H,br), 1.78–1.9 (2H,m), 2.9–3.0 (4H,m), 3.3–3.44 (4H,m), 7.78 (2H,d),

EXAMPLE 17

Using the method described in Example 7 but using 4-chloro-2,6-dimethylpyrimidine there was obtained 1-(4-bromophenylsulphonyl)-4-[1-(2,6-dimethylpyrimidin-4-yl)-4 -piperidylcarbonyl]homopiperazine as a foam; NMR ($CDCl_3$): 1.7–1.9 (m, 4H), 1.9–2.03 (m, 2H), 2.32 (s, 3H), 2.48 (s, 3H), 2.6–2.75 (m, 1H), 2.84–2.98 (m,2H), 3.22–3.37 (m, 3H),3.4–3.46 (m, 1H), 3.6–3.75 (m, 4H), 4.4–4.5 (m,2H), 6.2 (s, 1 H), 7.6–7.7 (m, 4H).

EXAMPLE 18

Using the method described in Example 7 but with 4-chloro-6-methylpyrimidine there was obtained 1-(4-bromophenylsulphonyl)-4-[1-(6-methylpyrimidin-4-yl)-4-piperidylcarbonyl]homopiperazine as a foam: NMR ($CDCl_3$): 8 1.7–1.9(m, 4H), 1.92–2.05 (m, 2H), 2.36 (s, 3H), 2.64–2.78 (m, 1H), 2.88–3.01 (m, 2H), 3.22–3.37 (m, 3H), 3.4–3.46(m, 1H), 3.62–3.76 (m, 4H), 4.4–4.5 (m, 2H), 6.38(s, 1H), 7.6–7.7 (m,4H), 8.5 (s, 1H).

EXAMPLE 19

Using a procedure analogous to that described in Example 16 with 1-(4-pyrimidinyl)-4-methyl-4-(ethoxycarbonyl)piperidine, lithium hydroxide, thionyl chloride and 1-(4-bromophenylsulphonyl)piperidine, there was obtained 1-(4-bromophenylsulphonyl)-4-[1-(4-pyrimidinyl)-4-methylpiperidin-4-ylcarbonyl]piperazine as a solid, m.p. 217–218° C.; NMR ($CDCl_3$): 1.3 (s, 3H), 1.5–1.6 (m, 2H), 2.15–2.28 (m, 2H), 3.0–3.08 (m, 4H), 3.32–3.42 (m,2H), 3.7–3.92 (m, 6H), 6.44 (d, 1H), 7.68 (dd, 4H), 8.17 (d, 1H), 8.57 (s, 1H)

The starting material was prepared as follows.

1-(4-pyrimidinyl)-4-(ethoxycarbonyl)piperidine (400 mg) in 4 ml tetrahydrofuran was cooled to −70° C and treated with a solution of lithium diisopropylamide (1.0 ml in THF), under an argon atmosphere. After stirring 1.5 hours 1.2 ml of a solution of 1 ml iodomethane in 10 ml THF was added and reaction mixture left to reach room temperature overnight. Water added and extracted twice with ethyl acetate. Organic extract washed with brine and dried over magnesium sulphate, filtered and evaporated to give 1-(4-pyrimidinyl)-4-methyl-4-(ethoxycarbonyl)piperidine (370 mg) as an oil; NMR (CDCl3): 1.24 (s, 3H), 1.28 (t, 3H), 1.38–1.51 (m,2H), 2.14–2.26 (m, 2H), 3.12–3.26 (m, 2H), 4.03–4.14 (m, 2H), 4.2(q,2H), 6.5 (dd, 1H), 8.17 (d. 1H), 8.57 (s, 1H)

EXAMPLE 20

Using a procedure analogous to that described in Example 4, and the appropriate sulphonyl chloride, there was obtained the following compounds.

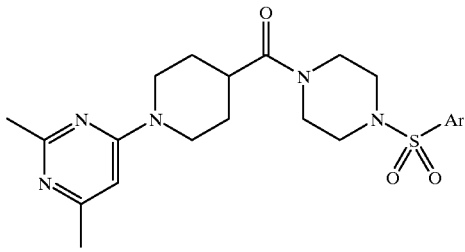

| Compound No. | Ar | mp °C. | NMR |
|---|---|---|---|
| 1 | 4-FC$_6$H$_4$ | foam | (300MHz, CDCl$_3$) 7.8(d, 2H), 7.3(d, 2H), 6.22(s, 1H), 4.41(d, 2H), 3.72(d, 4H), 3.0(broad s, 4H), 2.96–2.94(m, 2H), 2.75–2.65(m, 1H), 2.45 (s, 3H), 2.30(s, 3H), 1.75–1.65(m, 4H). |
| 2 | Phenyl | 149.1 | (300MHz, CDCl$_3$) 7.75–7.65(m, 3H), 7.63–7.58 (m, 2H), 6.45(s, 1H), 4.31(d, 2H), 3.6(d, 4H), 2.90–2.85(m, 7H), 2.3(s, 3H), 2.21(s, 3H), 1.62 (d, 2H), 1.27–1.33(m, 2H). |
| 3 | 4-ClC$_6$H$_4$ | 198.7 | (300MHz, CDCl$_3$) 7.7(d, 2H), 7.5(d, 2H), 6.21(s, 1H), 4.42(d, 2H), 3.71(d, 4H), 3.0(s, 4H), 2.94–2.87(m, 2H), 2.72–2.68(m, 1H), 2.45 (s, 3H), 2.31(s, 3H), 1.75–1.65(m, 4H). |
| 4 | 4CF$_3$C$_6$H$_4$ | foam | (300MHz, CDCl$_3$) 7.9(d, 2H), 7.82(d, 2H), 6.19(s, 1H), 4.40(d, 2H), 3.71(broad d, 4H), 3.05 (broad s, 4H), 2.95–2.84(m, 2H), 2.75–2.62 (m, 1H), 2.5(s, 3H), 2.31(s, 3H), 1.85–1.65 (m, 4H). |
| 5 | 2Cl-4CF$_3$C$_6$H$_3$ | foam | (300MHz, CDCl$_3$) 8.21(d, 1H), 7.81(s, 1H), 7.72(d, 1H), 6.23(s, 1H), 4.4(d, 2H), 3.72(broad s, 4H), 3.38(d, 4H), 3.05–2.95(m, 2H), 2.8–2.7(m, 1H), 2.51(s, 3H), 2.35(s, 3H), 1.85–1.75(m, 3H). |

The starting materials were prepared as follows.

1-(2,6-dimethylpyrimidin-4-yl)-4-(ethoxycarbonyl) piperidine (10 g) as a solution in THF (100 ml) and methanol (50 ml) was treated with lithium hydroxide (3.2 g) in water (50 ml). The reaction was stirred for 2 hours at room temperature, evaporated and azeotroped with toluene (2×100 ml). The remaining crude solid was treated with thionyl chloride (100 ml) and stirred at room temperature overnight. Thionyl chloride was removed in vacuo and the crude acid chloride was azeotroped with toluene (2×ml).

The crude acid chloride was suspended in dichloromethane (100 ml), to which was added 1-(tert-butoxycarbonyl)piperazine (7.1 g) in dichloromethane (100 ml) over 10 minutes, followed by triethylamine (20 ml). The reaction was stirred at room temperature overnight. Solvent was removed in vacuo and the product was purified by flash chromatography (silica; 10% methanol in dichloromethane) to give 1-(tert-butoxycarbonyl)-4-[1-(2,6-dimethylpyrimidin-4-yl)-4-piperidylcarbonyl]piperazine an oil (14.1 g); NMR (CDCl$_3$): 1.51 (s, 9H), 1.75–1.85 (m, 4H), 2.3 (s, 3H), 2.5 (s, 3H), 2.75–2.80 (m, 1H), 2.85–3.00 (m, 2H), 3.35–3.65 (m, 8H), 4.43 (d, 2H), 6.21 (s, 1H).

2,6-Dimethyl-4-chloro-pyrimidine (1.0 g) in ethanol (10 ml) was added slowly to a solution of ethyl isonipecotate (1.1 g) and triethylamine (2.0 ml) in ethanol (20 ml). The reaction was stirred at room temperature overnight. The solvent was removed in vacuo and the residue was partitioned between ethyl acetate and water, washed with water (2×50 ml), dried and evaporated to give 1-(2,6-dimethylpyrimidin-4-yl)-4-(ethoxycarbonyl)piperidine as an oil (1.71 g); NMR (CDCl$_3$): 1.25 (t, 3H), 1.65–1.80 (m, 4H), 1.95–2.00 (m, 2H), 2.55 (s, 3H), 2.45 (s, 3H), 2.50–2.60 (m, 1H), 3.00 (dt, 2H), 4.15 (q, 2H), 4.35 (d, 2H), 6.2 (s, 1H).

2,4-Dimethyl-6-hydroxypyrimidine (20 g) was added to phosphorus oxychloride (120 ml) and the mixture was refluxed for 2 hours. Excess phosphorus oxychloride was removed in vacuo, water was added and the product was extracted into dichloromethane (2×200 ml), dried (Na2SO4) and the solvent removed to give 2,6-dimethyl-4-chloropyrimidine as an oil (21 g) which slowly crystallised on standing; NMR (CDCl$_3$): 2.52 (s, 3H), 2.71 (s, 3H), 7.05 (s, 1H).

EXAMPLE 21

Using an analogous procedure to that described in Example 27 but with 2,6-dimethyl-4-chloropyrimidine as starting material there was obtained 1-(4-chlorophenylsulphonyl)-4-(1 -(2.6-dimethylpyrimidin-4-yl)-4-piperidylcarbonyl]homopiperazine as a foam; NMR (DMSOd$_6$): 1.15–1.70 (m, 6H), 2.03 (s, 3H), 2.13 (s, 3H), 2.60–2.82 (m, 3H), 3.05–3.55 (m, 8H), 4.10–4.30 (m, 2H), 6.32 (s, 1H), 7.45–7.55 (m, 2H), 7.60–7.68 (m, 2H).

EXAMPLE 22

Using an analogous procedure to that described in Example 7 and with chloro-benzene starting materials in place of bromo-benzene starting material and using 2-methyl-4-chloropyrimidine in place of 4-chloropyrimidine there was obtained 1-(4-chlorophenylsulphonyl)-4-[1-(2-methylpyrimidin-4-yl)-4-piperidylcarbonyl]homopiperazine as a foam: NMR (DMSOd$_6$): 1.35–1.90 (m, 6H), 2.35 (s, 3H), 2.80–3.05 (m, 3H), 3.20–3.75 (m, 8H), 4.30–4.40 (m, 2H), 6.60 (dd. 1H), 7.65–7.75 (m, 2H), 7.75–7.85 (m, 2H).

The 1-(4-chlorophenylsulphonyl)-4-(1-tert-butoxycarbonylpiperidin-4-ylcarhonyl)homopiperazine intermediate was isolated as a foam: NMR (DMSOd$_6$): 1.25–1.85 (m, 6H), 1.40 (s, 9H), 2.65–2.85 (m, 3H), 3.20–3.65 (m, 8H), 3.85–4.9 (m, 2H), 7.60–7.70 (m, 2H), 7.75–7.85 (m, 2H).

EXAMPLE 23

Using a similar procedure to that described in Example 7 but using 2-methyl-4-chloropyrimidine in place of 4-chloropyrimidine there was obtained 1-(4-bromophenylsulphonyl)-4-[1-(2-methylpyrimidin-4-yl)-4-piperidylcarbonyl]homopiperazine as a foam: NMR (DMSOd$_6$): 1.35–1.85 (m, 6H), 2.35 (s, 3H), 2.75–3.0 (m, 3H), 3.2–3.70 (m, 8H), 4.30–4.45 (m, 2H), 6.60 (d, 1H), 7.65–7.85 (m, 4H), 8.05 (d, 1H).

EXAMPLE 24

Using the procedure described in Example 16 with phenylsulphonyl chloride there was obtained 1-(phenylsulphonyl)-4-[]-(4-pyrimidinyl)-4-piperidylcarbonyl]homopiperazine as a gum:

NMR (DMSOd$_6$): 1.3–1.8 (m, 6H), 2.75–3.0 (m, 3H), 3.15–3.55 (m, 8H), 4.25–4.40 (m, 2H), 6.75 (dd, 1H), 7.50–7.65 (m, 3H), 7.65–7.75 (m, 2H), 8.08 (d, 1H), 8.40 (s, 1H).

The 1-(phenylsulphonyl)homopiperazine intermediate was isolated as an oil;

NMR (DMSOd$_6$): 1.40–1.55 (m, 2H), 2.45–2.60 (m, 4H), 2.85–3.20 (m, 4H), 7.35–7.55 (m, 5H).

EXAMPLE 25

Ethyl acetate saturated with gaseous HCl was added to a solution of 1-(4-chlorophenylsulphonyl)-4-[1-(t-butoxyoxycarbonyl)piperazine-4-ylcarbonyl]piperidine (1.10 g) in ethyl acetate (25 ml). The reaction was stirred at room temperature for 2 hours. Solvent was removed by evaporation to give the crude 1-(4-chlorophenylsulphonyl)-4-(4-piperazinylcarbonyl)piperidine hydrochloride.

The crude 1-(4-chlorophenylsulphonyl)-4-(piperazin-4-ylcarbonyl)piperidine hydrochloride, 2-methyl-4-chloro-pyrimidine (299 mg) and triethylamine (1.47 ml) were heated under reflux in ethanol (12 ml) for 5 hours. The solvent was removed by evaporation. Purification by filtration column chromatography (silica) eluting with 2% methanol/dichloromethane increasing to 10% methanol/dichloromethane gave 1-(4-chlorophenylsulphonyl)-4-[1-(2-methylpyrimidin-4-yl)piperazin-4-ylcarbonyl]piperidine as a solid (0.87 g); NMR (CDCl$_3$): 1.7–2.0 (m, 5H), 2.5 (m, 5H), 3.5–3.8 (m, 10H), 6.3 (m, 1H), 7.5 (m, 2H), 7.7 (m, 2H), 8.2 (m, 1H).

The 1-(4-chlorophenylsulphonyl)-4-(1-(t-butoxycarbonyl)piperazin-4-ylcarbonyl)piperidine used as starting material was prepared as follows.

4-Chlorophenylsulphonyl chloride (18 g) was added slowly to an icebath cooled solution of isonipecotic acid (10 g) and triethylamine (22.65 ml) in dichloromethane (500 ml). After addition was completed the reaction was allowed to warm to room temperature and stirred overnight. The reaction mixture was washed with water (2×2(0 ml), and reduced in vacuo to give the crude acid as a red oil.

Thionyl chloride (5 ml) was added to the above crude acid and the reaction was refluxed for 2 hours. The reaction was evaporated in vacuo to give the crude acid chloride.

1-(tert-butoxycarbonyl)-piperazine (1.44 g) was added to a solution of the crude acid chloride in dichloromethane (25 ml). The reaction was stood at room temperature overnight. The reaction was then reduced in vacuo. The product was purified by filtration column chromatography (silica) eluting initially with dichloromethane with increasing concentrations of ethyl acetate (up to 20%). Trituration with ether and hexane gave a solid (1.15 g); NMR (CDCl$_3$): 1.45 (s, 9H), 1.75 (m, 2H), 1.9 (m, 2H), 3.35–3.6 (m, 8H), 2.45 (m, 2H), 3.75 (m, 2H), 7.5 (m, 2H), 7.7 (m, 2H).

EXAMPLE 26

Using a similar procedure to that described in Example 27 there was prepared 1-(4-bromophenylsulphonyl)-4-[1-(2-methylpyrimidin-4-yl)piperazin-4-ylcarbonyl]piperazine, as a solid mpt 219–220° C.; NMR (CDCl$_3$): 2.5 (s, 3H), 3.05 (m, 4H), 3.3 (m, 4H), 3.4(m, 4H), 3.65 (m. 4H), 6.3 (m, 1H), 7.6 (m, 2H), 7.7 (m, 2H), 8.15 (m, 1H).

The following intermediates were isolated: 1-(4-bromophenylsulphonyl)-4-[1-(tert-butoxycarbonyl)piperazin-4-ylcarbonyl]piperazine:

NMR (CDCl$_3$): 1.45 (s, 9H), 3.0 (m, 4H), 3.15 (m. 4H), 3.4 (m, 8H), 7.6 (m, 2H), 7.7 (m, 2H).

1-(4-bromophenylsulphonyl)-4-(4-nitrophenyloxycarbonyl)piperazine; NMR (CDCl$_3$): 3.1 (m, 4H), 3.6–3.8 (m, 4H), 7.25 (m, 2H), 7.65 (m, 2H), 7.7 (m, 2H), 8.25 (m, 2H).

EXAMPLE 27

Ethyl acetate saturated with gaseous HCl was added to a suspension of 1-(4-bromoplienylsulphonyl)-4-(1-(tert-butoxycarbonyl)piperazin-4-ylcarbonyllhomopiperazine (1.2 g) in ethyl acetate (20 ml). After stirring overnight the reaction was evaporated in vacuo to give the amine hydrochloride as a white solid (1.31 g). This material was used directly without purification.

Triethylamine (1.88 ml) was added to a suspension of the crude amine hydrochloride (1.3 g) in ethanol (20 ml). 4-chloro-2-methyl-pyrimidine (318 mg) was added and the reaction was refluxed for 3 hours. The reaction was evaporated in vacuo.

Purification by suction chromatography (silica; gradient elution, dichloromethane to 7.8% methanol in dichloromethane) gave 1-(4-bromophenylsulphonyl)-4-[1-(2-methylpyrimidin-4-yl)piperazin-4-ylcarbonyl]homopiperazine as a gum (1.31 g); NMR (CDCl$_3$): 2.0 (m, 2H), 2.55 (s, 3H), 3.30 (m, 6H), 3.35–3.55 (m, 6H), 3.7 (m, 4H), 6.4 (s, 1H), 7.65 (s, 4H), 8.15 (s, 1H).

The starting material was prepared as follows.

Triethylamine (11.5 ml) was added to a suspension of 1-(4-bromophenylsulphonyl)-4-(4-nitrophenyloxycarbonyl)homopiperazine (4.0 g) in DMF (50 ml). 1-(tert-butoxycarbonyl)piperazine (1.54 g) was added and the reaction was heated at 110° C. for 70 hours. The reaction mixture was evaorated in vacuo.

Purification by suction chromatography (silica; gradient elution, hexane to ethyl acetate) gave 1-(4-bromophenylsulphonyl)-4-[1-(t-butoxycarbonyl)piperazin-4-ylcarbonyl]homopiperazine (1.28 g); NMR (CDCl$_3$): 0.45 (s, 9H), 2.0 (m, 2H), 3.1 (m, 4H), 3.3 (m, 2H), 3.45 (m, 10H), 7.65 (s, 2H)

4-Nitrophenylchloroformate (3.31 g) was added to an ice bath cooled solution of the amine (5.0 g) and triethylamine (2.4 ml) in dichloromethane (200 ml). After stirring for 10 minutes the reaction was allowed to room temperature and stirred for a further 1 hour. The reaction mixture was evaporated in vacuo.

Purification by suction chromatography (silica; gradient elution, hexane to ethyl acetate, and finally with methanol:ethyl acetate:dichloromethane [1:4:5]) gave 1-(4-bromophenylsulphonyl)-4-(4-nitrophenyloxycarbonyl) homopiperazine; as a yellow solid (4.29 g); NMR (CDCl$_3$): 2.05 (m, 2H), 3.3–3.5 (m, 4H), 3.6–3.8 (m, 4H), 7.25 (m, 2H), 7.65 (s, 4H), 8.25 (m, 2H).

EXAMPLE 28

Using a similar procedure to that described in Example 3 the following compounds were prepared.

(500 ml) and triethylamine (41 ml) overnight. The solvent was evaporated and the residue was dissolved in dichloromethane and washed with water. The organic phase was dried (Na$_2$SO$_2$), and evaporated to give 2-methyl-4-chloro-6-[1-(tert-butoxycarbonyl]piperazin-4-yl)pyrimidine as a solid (41.5 g); NMR (CDCl$_3$): 6.35 (s, 1H), 3.65 (m, 4H), 3.5 (m, 4H), 2.5 (s, 3H), 1.45 (s, 9H).

A mixture of 2-methyl-4-chloro-6-[1-(tert-butoxycarbonyl)piperazin-4-yl]pyrimidine (41.40 g), ethanol (500 ml) and 2 g of catalyst (30% palladium on carbon)

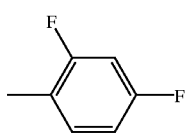

| Comp. No. | X | R | mp °C. | $^1$HNMR |
|---|---|---|---|---|
| 1 | H | 4-F-phenyl | 146–149 | $^1$H-NMR(200/250MHz)(CDCl$_3$): δ(ppm) 1.82(m, 2H), 1.94(m, 2H), 2.50(m, 3H), 3.51–3.79(m, 10H), 6.50(d, 1H), 7.24 (m, 2H), 7.79(m, 2H), 8.25(d, 1H), 8.62 (s, 1H). |
| 2 | H | phenyl | 177–179 | $^1$N-NMR(200/250MHz)(CDCl$_3$): δ(ppm) 1.75–2.20(m, 4H), 2.49(m, 3H), 3.49–3.78 (m, 10H), 6.50(d, 1H), 7.50–7.61(m, 3H), 7.80(m, 2H), 8.25(d, 1H), 8.60(s, 1H). |
| 3 | 2,6 dimethyl | 4 Br Phenyl | 173–174 | 1.75(m, 4H), 2.3(s, 3H), 2.5(s, 3H), 2.7(m, 1H), 2.9(m, 2H), 3.1(m, 4H), 3.7(m, 4H), 4.4(m, 2H), 6.2(s, 1H), 7.6–7.8(dd, 4H) |
| 4 | H | 4 CF$_3$ Phenyl | 201–202 | 1.75(m, 4H), 2.7(m, 1H), 2.9(m, 2H), 3.1(m, 4H), 3.7(m, 4H), 4.4(m, 2H), 6.5(d, 1H), 7.8–7.9(dd, 4H), 8.2(d, 1H), 8.6(s, 1H) |
| 5 | 6 Me | 4 Br Phenyl | 166–167 | 1.75(m, 4H), 2.3(s, 3H), 2.7(m, 1H), 2.9(m, 2H), 3.1(m, 4H), 3.7(m, 4H), 4.4(m, 2H), 6.4(s, 1H), 7.6–7.7(dd, 4H), 8.5(s, 1H) |
| 6 | 2,6-Me | 4 CL Phenyl | Foam | 1.65–1.85(4H, m), 1.85–2.00(1H, m), 2.35(s, 3H), 2.41–2.60(m, 6H), 3.40–3.61(4H, m), 3.61–3.80(m, 5H), 6.20(s, 1H), 7.52(d, 2H), 7.75(d, 2H). |
| 7 | 2 Me | 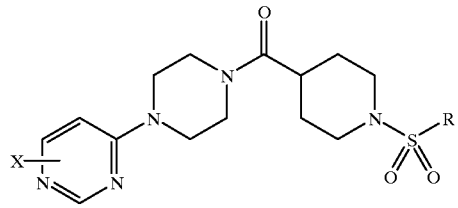 | | (CDCl$_3$) 1.77, m, 4H; 2.48, s, 3H; 2.71, m, 1H; 2.93, m, 2H; 3.24, bs, 4H; 3.67, bs, 4H; 4.42, dt, 2H; 6.31, d, 1H; 6.98, m, 2H; 7.87, m 1H; 8.12, d, 1H |

EXAMPLE 29

1-(tert-butoxycarbonyl)-4-(1-(2-methylpyrimidin-4-yl) piperazin-4-ylcarbonyl)piperazine (700 mg) was stirred in dichloromethane (20 ml) and triethylarnine (1.34 ml) and cooled in an ice-bath. 4-chlorobenzenesulphonylchloride (0.56 g) was added and reaction allowed to warm to room temperature and then stirred overnight. The mixture was evaporated and the residue was purified by chromatography on silica gel using in gradient of dichloromethane to 8% methanol in dichloromethane as eluent to give a foam. This was triturated with diethylether to give 1-(4-chlorophenylsulphonyl)-4-[1-(2-methylpyrimidin-4 -yl) piperazin-4-ylcarbonyl]piperazine a colourless solid 1.05 g ;m.p. 183–184° C.; NMR (CDCl$_3$): 8.15 (m, 1H), 7.7 (m, 2H), 7.55 (m, 2H), 6.3 (m, 1H), 3.65 (m, 4H), 3.45 (m, 4H), 3.35 (m, 4H), 3.05 (m, 4H), 2.5 (s, 3H).

The starting material was prepared as follows.

Dichloropyrimidine (24.79 g) and 1-(tert-butoxycarbonyl)piperazine (27.41 g) were stirred in ethanol and was stirred under hydrogen for 72 hours. The mixture was filtered through diamataceous earth and the filtrate evaporated to give 2-methyl-4-(1-(tert-butoxycarbonyl) pyrimidine as a solid (36.13 g); NMR (CDCl$_3$): 8.2 (m, 1H), 6.85 (m, 1H), 3.9 (bm, 4H), 3.6 (m, 4H), 2.75 (s, 3H), 1.5 (s, 9H), 2-methyl-4-(1-(tert-butoxycarbonyl)pyrimidine (36.13 g) was suspended in ethyl acetate (200 ml) and then saturated solution (200 ml) of hydrogen chloride in ethyl acetate was added. The mixture was stirred overnight and then evaporated to give 2-methyl-4-(1-piperazinyl)pyrimidine hydrochloride as a white powder (44.80 g); NMR (CDCl$_3$): 8.35 (d, 1H), 7.15 (d, 1H), 2.55 (s, 3H), 3.8–4.4 (bm, 8H).

2-Methyl-4-(1-piperazinyl)pyrimidine hydrochloride (18.80 g) and 1-(tert-butoxycarbonyl)-4-(4-nitrophenyloxycarbonyl) piperazine (25 g) were stirred in dry DMF (250 ml) and triethylamine (40 ml) under argon. The reaction mixture was stirred at 110° C. for 5 hours and then allowed to cool overnight. The solid was collected by filtration, washed with DMF and isohexane. The solid was purified by chromatography on silica gel using a gradient of dichloromethane to 5% methanol in dichloromethane as eluent to give 1-(tert-butoxycarbonyl)-4-(1-(2-methylpyrimidin-4-yl)piperazin-4-ylcarbonyl)piperazine as a pale solid (19.92g); NMR (CDCl$_3$): 8.15 (m, 1H), 6.35 (m, 1H), 3.7 (m, 4H), 3.45 (m, 4H), 3.35 (m, 4H), 3.3 (m, 4H), 2.5 (s, 3H), 1.45 (s, 9H).

The crude 1-(tert-butoxycarbonyl-4-(1-(2-methylpyrimidin-4-yl)piperazin-4-ylcarbonyl)piperazine (19.9 g) was suspended in ethyl acetate (200 ml) and then a saturated solution (100 ml) of hydrogen chloride in ethyl acetate was added and reaction mixture was stirred overnight. The reaction mixture was evaporated to give a solid which was purified by chromatography using a gradient of dichloromethane to 10% methanol in dichloromethane to give a product which was partitioned between dichloromethane and water. The organic layer was separated, dried (Na$_2$SO$_4$) and evaporated to give 1-(tert-butoxycarbonyl)-4-(1-(2-methylpyrimidin-4-yl)piperazin-4-ylcarbonyl) piperazine; m.p. 212–213° C.; NMR (CDCl$_3$) 8.15 (m, 1H), 6.3 (m, 1H), 3.65 (m, 4H), 3.35 (m, 4H), 3.3 (m,4H), 2.9 (m, 4H), 2.5 (s, 3H).

EXAMPLE 30

A mixture of 4-nitrophenyl chloroformate (32.35 g), 1-(tert-butoxycarbonyl)piperazine (28.48 g) and triethylamine (23.4 ml) was stirred in dichloromethane (100 ml) overnight. The solvent was removed by evaporation to give a yellow solid which was purified by filtration chromatography using hexane followed by ethyl acetate and then a gradient 5% to 10% methanol in dichloromethane as eluent to give 1-(t-butoxycarbonyl)-4-(4-nitropphenyloxycarbonyl)piperazine as a solid (56.6 g); NMR (CDCl$_3$): 8.25 (m, 2H), 7.3 (m, 2H), 3.5–3.7 (m, 8H) and 1.5 (s, 9H).

A mixture of 1-(t-butoxycarbonyl)-4-(4-nitrophenyloxycarbonyl)piperazine (25 g) and 1-(4-bromophenylsulphonyl)piperazine (16.87 g) was stirred in dry DMF (300 ml) overnight under an atmosphere of argon. The solvent was removed by evaporation. The residue was dissolved in dichloromethane, washed with water and aqueous sodium hydrogen carbonate solution. The organic phase was separated and evaporated to give a residue which was purified by chromatography using a gradient of hexane containing increasing amounts of ethyl acetate as eluent to give 1-(4-bromophenylsulphonyl)-4-[1-(tert-butoxycarbonyl)piperazin-4-ylcarhonyl]piperazine as a solid (18.02 g); NMR (CDCl$_3$): 7.7 (m, 2H), 7.6 (m, 2H), 3.4 (m, 8H), 3.2 (m, 4H), 3.05 (m, 4H), 1.45 (s, 9H).

A solution (200 ml) of ethyl acetate saturated with hydrogen chloride was added to a mixture of 1-(4-bromophenylsulphonyl)-4-[1-(t-butoxycarbonyl)piperazin-4-ylcarbonyl]piperazine and ethyl acetate (200 ml) . The mixture was stirred overnight. The solvent was removed by evaporation to give 1-(4-bromophenylsulphonyl)-4-(1-piperazinylcarbonyl)piperazine hydrochloride (16.30 g).

4-Methyl-6-chloropyrimidine (0.51 g) was added to a stirred mixture of 1-(4-bromophenylsulphonyl)-4-(1-piperazinylcarbonyl)piperazine hydrochloride (1.50 g) and ethanol (35 ml). Triethylamine (2.2 ml) was added and the mixture was heated at reflux for 6 hours. The solvent was removed by evaporation and the residue was purified by chromatography on silica gel using a gradient of 0% to 10% methanol in dichloromethane as eluent to give a foam. This was crystallised from methyl tert-butyl ether to give 1-(4-bromophenylsulphonyl)-4-[1-(4-methylpyrimidin-6-yl) piperazin-4-ylcarbonyl]piperazine as a solid (0.77 g); m.p. 215–216° C.; NMR (CDCl$_3$): 8.5 (s, 1H), 7.7 (m, 2H), 7.6 (m, 2H), 6.35 (s, 1H), 3.6 (m, 4H), 3.4 (m, 4H), 3.3 (m, 4H), 3.05 (m, 4H), 2.33 (s, 3H).

EXAMPLE 31

Using a similar method to that described in Example 3 the following compounds were prepared.

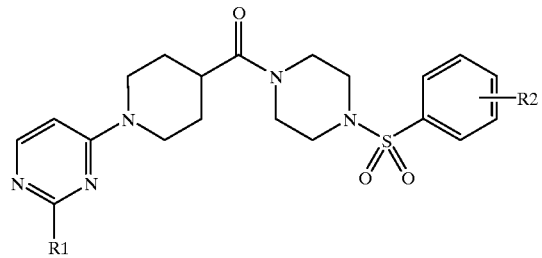

| Comp. No | R$^1$ | R$^2$ | m.p. (° C.) | NMR |
|---|---|---|---|---|
| 1 | R = n-propyl | R$^2$ - = 4-Br | Foam | 0.96(t, 3H), 1.75(m, 6H), 2.66(m, 3H), 2.925(m, 2H), 3.033(bs, 4H), 3.675(bd, 4H), 4.425(bd, 2H), 6.30(d, 1H), 7.62(d, 2H), 7.71(d, 2H), 8.125(d, 1H). |
| 2 | R$^1$ = ethyl | R$^2$ = 4-Br | Foam | 1.30(m, 3H), 1.76(m, 4H), 2.74(m, 3H), 2.96(m, 2H), 3.04(bs, 4H), 3.70(bd, 4H), 4.43(bd, 2H), 6.30(m, 1H), 7.62(m, 2H), 7.72(m, 2H), 8.14(m, 1H). |
| 3 | R$^1$ = CH$_3$ | R$^2$ = 4-Br | Foam | 1.81(m, 4H), 2.50(s, 3H), 2.79(m, 1H), 2.966(m, 2H), 3.633(bm, 8H), 4.46(bd, 2H), 6.33(d, 1H), 7.30(d, 2H), 7.585(d, 2H), 8.11(d, 1H). |

-continued

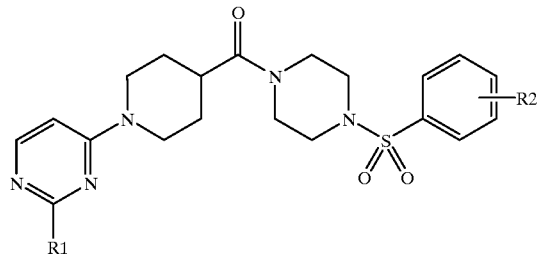

| Comp. No | R¹ | R² | m.p. (° C.) | NMR |
|---|---|---|---|---|
| 4 | R¹ = CH₃ | R² = 4-Cl | 187.6° C. | 1.70(m, 4H), 2.48(s, 3H), 2.66(m, 1H), 2.925(m, 2H), 3.04(bs, 4H), 3.66(bd, 4H), 4.40(bm, 2H), 6.30(d, 1H), 7.54(d, 2H), 7.68(d, 2H), 8.10(d, 1H). |
| 5 | R¹ = CH₃ | R² = 4-F | Foam | 1.75(m, 4H), 2.466(s, 3H), 2.68(m, 1H), 2.933(m, 2H), 3.05(bs, 4H), 3.68(bd, 4H), 4.40(bm, 2H), 6.30(d, 1H), 7.25(m, 2H), 7.875(m, 2H), 8.10(d, 1H). |
| 6 | R¹ = CH₃ | R² = 3-Cl, 4-F | 142.7° C. | 1.73(m, 4H), 2.475(s, 3H), 2.70(m, 1H), 2.925(m, 2H), 3.06(bs, 4H), 3.70(bm, 4H), 4.40(bm, 2H), 6.30(d, 1H), 7.33(t, 1H), 7.46(m, 1H), 7.84(dd, 1H), 8.10(d, 1H). |
| 7 | R¹ = CH₃ | R² = 3-F | 190° C. | 1.76(m, 4H), 2.50(s, 3H), 2.70(m, 1H), 2.95(m, 2H), 3.066(bs, 4H), 3.70(bd, 4H), 4.42(bd, 2H), 6.3(d, 1H), 7.35(cm, 1H), 7.45(cm, 1H), 7.55(m, 1H), 8.10(d, 1H). |
| 8 | R¹ = CH₃ | R² = 4-CF₃ | decomposed | 1.745(m, 4H), 2.466(s, 3H), 2.675(m, 1H), 2.94(m, 2H), 3.075(bs, 4H), 3.675(bd, 4H), 4.40(bd, 2H), 6.30(d, 1H), 7.833(d, 2H), 7.90(d, 2H), 8.10(d, 1H). |

EXAMPLE 32

Using a procedure analogous to that described in Example 3 the following compounds were prepared.

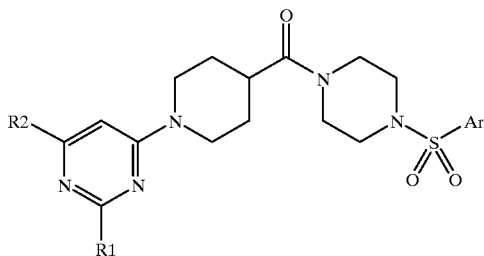

| No | R¹ | R² | Ar | m.p. (° C.) | NMR |
|---|---|---|---|---|---|
| 1 | Me | H | 4-CF₃ phenyl | Foam | 1.75–2.00(4H, m), 2.45(3H, s), 2.5–2.6(3H, m), 3.51–3.60(4H, m), 3.6–3.75(4H, m), 3.77–3.86(2H, m), 6.30(1H, d), 7.8(2H, d), 7.9(2H, d), 8.21(2H, d). |
| 2 | Me | Me | 4-chlorophenyl | 198.7 | 1.8–1.6(m, 4H), 2.26(s, 3H), 2.46(s, 3H), 2.75–2.60(m, 1H), 2.80–3.01(m, 2H), 3.05(broad s; 4H), 3.81–3.60(m, 4H), 4.41(d, 2H), 6.21(s, 1H), 7.55(d, 2H), 7.70(d, 2H). |
| 3 | Me | Me | 4-CF₃ phenyl | Foam | 1.65–1.80(m, 4H), 2.31(s, 3H), 2.45(s, 3H), 2.60–2.75(m, 1H), 2.85–2.97(m, 2H), 3.0–3.15(m, 4H), 3.61–3.80(m, 4H), 4.4(d, 2H), 6.2(s, 1H), 7.81(d, 2H), 7.90(d, 2H). |

EXAMPLE 33

4-[1-(2-Methylpyrimidin-4-yl)-piperazin-4-ylcarbonyl] piperazine (0.90g, 3.10 mmol) was stirred in dichloromethane (25ml). 4-Cyanobenzoyl chloride (570mg, 3.41mmol) was added followed by triethylamine (0.52ml, 3.72mmol). The reaction was stirred overnight at room temperature and then reduced in vacuo affording an 1-(4-cyanobenzoyl)-4-[1-(2-metlhylpyrimidin-4-yl)-piperazin-4-ylcarbonyl]piperazine as an off white solid, 1.23 g (95%) mp201–202° C.

$^1$HNMR(CDCl$_3$) 8.15 (d, 1H), 7.75 (m, 2H), 7.50 (m, 2H), 6.3 (d, 2H), 3.2–3.9 (6M, 16H), 2.5 (s, 3H)

EXAMPLE 34

In an analogous method to example 33 1-(4-bromobenzyl)-4-[1-(2-methylpyrimidin-4-yl)-piperazin-4-ylcarbonyl]piperazine using 4-bromobenzyl bromide was produced as a gum in 85% yield $^1$HNMR (CDCl$_3$) 8.15(d, 1H), 7.45 (m, 2H), 7.2 (m, 2H), 6.3 (d, 1H), 3.65 (m, 4H), 3.4 (s, 2H), 3.3 (m, 8H), 2.5 (s, 3H), 2.45 (m, 4H).

EXAMPLE 35

Using a similar procedure to that described in Example 27 there was prepared 1-(4-bromophenylsulphonyl)-4-[1-(6-methylpyrimidin-4-yl)piperazin-4-ylcarbonyl]piperazine as a pale yellow solid.

The 1-(4-bromophenylsulphonyl)-4-(piperazin-4-ylcarbonyl)piperazine chloride salt (1.50 g) was suspended in ethanol (35 ml) and the 4-methyl-6-chloropyrimidine was added (0.51 g) followed by triethylamine (2.2 ml). Reaction was then refluxed for 6 hours and reduced in vacuo.

Residue chromatographed (silica) DCM to 10% methanol/dichloro methane affording the above compound 0.77 g, 57% yield, mp 215–216° C.

$^1$HNMR (CDCl$_3$) 8.5 (s, 1H), 7.7 (m, 2H) 7.6 (m, 2H), 6.35 (s, 1H), 3.6 (m, 4H), 3.4 (m, 4H) 3.3 (M, 4H), 3.05 (m, 4H), 2.35 (s, 3H).

EXAMPLE 36

In a similar process as described in Example 39 using 1-(2-ethylpyrimidin-4-yl)-4-methyl-piperidine-4-carboxylic acid and 1-(4-bromophenylsulphonyl)-piperazine the following was produced 1-(4-bromophenylsulphonyl)-4-[1-(2-ethylpyrimidin-4-yl)-4-methyl-piperidin-4-ylcarbonyl] piperazine.

Nmr: 1.28 (s, 3H), 1.3 (t, 3H), 1.5–1.6 (m, 2H), 2.18 (d, 2H), 2.74 (qt, 2H), 3.02 (br s, 4H), 3.38 (t, 2H), 3.73 (br s, 4H), 3.87 (d, 2H), 6.28 (d, 1H), 7.68 (dd, 4H), 8.13 (d, 1H).

The starting materials were prepared as follows:

1-(2-Ethylpyrimidin-4yl)-4-methyl-piperidine-4-carboxylic acid was prepared on a 3 mmol 4-methyl-4-ethoxycarbonyl-piperidine (as TFA salt) in 7 ml ethanol and 1 ml Et3N treated with a solution of 0.531 g 2-ethyl-4,6-dichloropyrimidine in 4 ml ethanol. After 20 hours at ambient temp. The ethanol was removed and the residue partitioned between water and ethanol, washed with sodium hydrogen carbonate solution and brine. Evaporated to give gum (88.3%).

Nmr: 1.23 (s, 3H), 1.27 (dt, 6H), 1.37–1.5 (m, 2H), 2.19 (d, 2H), 2.73 (qt, 2H), 3.12–3.23 (m, 2H), 4.06 (d, 2H), 4.2 (qt, 2H), 6.32 (s, 1H).

4-Methyl-4-ethoxycarbonyl-piperidine was prepared by alkylation of 1-(benzyloxycarbonyl)-4-ethoxycarbonyl-piperidine (J.Med.Chem 1994, 37, p 368)-2.6 g (10 mmol) 1. in 25 ml dry THF at –70° C., under argon, treated with 7 ml lithium di-isopropylamide solution (2M). Stirred 1.5 hours then a solution of 1.5 equivalents of alkyl halide in 5 ml of THF added dropwise. Reaction allowed to warm to ambient temperature over several hours, diluted with ethyl acetate and water. Aqueous layer extracted twice with ethyl acetate, organic solution washed with brine and dried. Evaporated to give the liquid product.

NMR: 0.82 (t, 3H), 1.27 (t, 3H), 1.45 (s, 9H), 1.56 (qt, 2H), 2.1 (d, 2H), 2.8–2.94 (m, 2H), 3.8–3.95 (d, 2H), 4.18 (qt, 2H).

EXAMPLE 37

1-(2-Methylpyrimidin-4yl)-4-ethyl-piperidine-4-carboxylic acid 2.03 g (8.16 mmol) was treated with 70 ml thionyl chloride, stirring for 1.5 hours at 25–35° C. The thionyl chloride was evaporated and the residue suspended in 50 ml dichloromethane and added to a solution of 2.49 g of 4-bromophenylsulphonylpiperazine in 80 ml dichloromethane containing 10 ml triethylamine and left to stir overnight. Washed with water and brine, dried, evaporated to an oil.

Chromatographed (Bondelut, dichloromethane then 1% methanol/dichloromethane/ 1% ammonium hydroxide), resultant gum dissolved in ethyl acetate, ether added to give 4-(bromophenylsulphonyl)-1-[1-(2-methylpyrimidin-4-yl)-4-ethyl-4-piperidylcarbonyl]piperazine a colourless solid 0.975 g, mp 170.5° C.

NMR: 0.8 (t, 3H), 1.43–1.57 (m, 2H), 1.65 (qt, 2H), 2.28 (d, 2H), 2.5 (s, 3H), 3.03 (t, 4H), 3.2–3.3 (m, 2H), 3.76 (t, 4H), 3.94 (d, 2H), 6.28 (d, 1H), 7.65 (dd, 4H), 8.08 (d, 1H).

EXAMPLE 38

1-(2-Methylpyrimidin-4-yl)-4-propen-2-yl-piperidine-4-carboxylic acid (1.98 g) acid stirred 18 hours with 70 ml thionyl chloride at ambient temperature the residue slurried in 50 ml dichloromethane and added to a solution of 1.9 g 4-bromophenylsulphonyl piperazine in 60 ml dichloromethane containing 10 ml triethylamine and stirred overnight. The dichloromethane was washed with water and brine, dried and evaporated to a gum which was chromatographed (Bondelut, dichloromethane then 1% methanol/dichloromethane/1% ammonium hydroxide) and product recrystallised from ethyl acetate/ether to give 1-(4-bromophenylsulphonyl)-4-[1-(2-methylpyrimidin-4-yl)-4-propen-2-yl-piperidin-4-ylcarbonyl]piperazine 1.12 g white solid mp 217° C.

Nmr: 1.52–1.64 (m, 2H), 2.24 (d, 2H), 2.36 (d, 2H), 2.47 (s, 3H), 3.03 (t, 4H), 3.2–3.32 (m, 2H), 3.7 (t, 4H), 3.92 (d, 2H), 4.98 (d, 1H), 5.04 (d, 1H), 5.52–5.66 (m, 1H), 6.23 (d, 1H), 7.65 (dd, 4H), 8.08 (d, 1H).

Starting materials were prepared in an analogous procedure as described in Example 47. 1-(2-Methylpyrimidin-4-yl)-4-propen-2-yl-piperidine-4-carboxylic acid was isolated.

NMR: 1.27 (t, 3H), 1.3–1.4 (m, 2H), 1.45 (s, 9H), 2.08 (d, 2H), 2.27 (d, 2H), 2.9 (t, 2H), 3.8–3.95 (d, 2H), 4.18 (qt, 2H), 5.0–5.1 (m, 2H), 5.6–5.76 (m, 1H).

EXAMPLE 39

1-(4-Bromophenylsulphonyl)-4methyl-piperidine-4-carboxylic acid (12.73 g) added to 120 ml thionyl chloride and stirred at 30–35° C. for 3 hours. The thionyl chloride was removed and residue dissolved in 150 ml dichloromethane and added dropwise over 30 minutes to a solution of 8.9 g of the 1-(2-methylpyrimidin-4-yl)piperazine in 170 ml dichloromethane containing 20 ml triethylamine. The mixture was stirred overnight, washed with water and brine, dried and evaporated to give 18.1 g beige solid. Recrystallised from ethyl acetate gave 1-(bromophenylsulphonyl)-4-[1-(2-methylpyrimidin-4-yl)piperazin-4-ylcarbonyl]-4-methyl-piperidine 12.6 g mp 213.6° C.

Nmr: 1.28 (s, 3H), 1.57–1.7 (m, 2H), 2.28 (d, 2H), 2.52 (s, 3H), 2.73 (t, 2H), 3.47 (d, 2H), 3.57–3.70 (m, 8H), 6.3 (d, 1H), 7.63 (dd, 4H), 8.18 (d, 1H).

Starting materials were prepared as follows:

1-(4-Bromophenylsulphonyl)-4-methyl-4-ethoxycarbonylpiperidine-1-(benzyloxycarbonyl)-4-methyl-4-ethoxycarbonyl-piperidine (12g) in 80 ml dichloromethane treated with 80 ml TFA. After 30 minutes the mixture was evaporated to dryness and dissolved in 250 ml THF and 26.5 ml triethylamine. A solution of 11.3 g 4-bromophenylsulphonyl chloride in 90 ml THF was added dropwise and the mixture was stirred. The THF was evaporated and the residue treated with sodiumhydrogen carbonate solution and extracted into dichioromethane. The mixture was washed with brine, dried, to give product in quantitative yield.

NMR: 1.15 (t, 3H), 1.16 (s, 3H), 1.47–1.6 (m, 2H), 2.17 (d, 2H), 2.45 (dt, 2H), 3.5 (d, 2H), 4.06 (qt, 2H), 7.63 (dd, 4H).

1(4-Bromophenylsulphonyl)-4-methyl-piperidine-4-carboxylic acid--17.3 g of 1-(4-Bromophenylsulphonyl)-4-methyl-4-ethoxycarbonylpiperidine in 200 ml THF refluxed 2 hours with a solution of 11.3 g lithium hydroxide in 70 ml water/70 ml ethanol. The organic solvent was evaporated, water added the aqueous solution extracted with ether. The aqueous phase was made acid by adding concentrated HCl. The resulting solid was filtered, washed and dried to give 12.73 g of the product (79.3% yield)

NMR: 1.21 (s, 3H), 1.5–1.63 (m, 2H), 2.16 (d, 2H), 2.6 (t, 2H), 3.5 (d, 2H), 7.64 (dd, 4H).

EXAMPLE 40

1-(4-Bromophenylsulphonyl)-4-(1-t-butyloxycarbonyl-4-methyl-4-piperidylcarbonyl)piperazine 0.616 g in 5 ml dichloromethane treated with 6 ml trifluoroacetic acid for 1.5 hours and the mixture evaporated to dryness. Residue dissolved in 10 ml ethanol and 3 ml triethylamine and a solution of 2-methyl-4-chloropyrimidine, 180 mg (1.2 equivalents), in 3 ml ethanol added and heated at reflux for 2 hours. Residue dissolved in ethyl acetate, washed with sodium bicarbonate solution followed by brine then evaporated. The solid product was chromatographed on Bondelute (dichloromethane then 1% methanol/dichloromethane/1%ammonium hydroxide) to give 1-(4-bromophenylsulphonyl)-4-[1-(2-methyl-pyrimidin-4-yl)-4-methyl-4-piperidylcarbonyl]piperazine 360 mg solid.

Nmr: 1.28 (s, 3H), 1.48–1.6 (m, 2H), 2.19 (d, 2H), 2.47 (s, 3H), 3.03 (t, 4H), 3.3–3.42 (m, 2H), 3.75 (t, 4H), 3.84 (d, 2H), 6.27 (d, 1H), 7.66 (dd, 4H), 8.05 (d, 1H).

The starting materials were prepared as follows-1-benzyloxycarbonyl-4-methyl-piperidine-4-carboxylic acid in 6 ml THF treated, under argon, with a solution of 0.82 g 1,1'-carbonyldiimidazole in 15 ml THF and stirred for 1 hour. 1.53 g 4-bromophenylsulphonyl piperazine in 10 ml THF/5 ml dichloromethane added and stirred overnight. Solvent removed and residue partitioned between ethyl acetate and water, washed with brine, dried and evaporated. Chromatographed (Bondelute, dichloromethane then 2% methanol/dichloromethane/1% ammonium hydroxide) to give 0.616 g solid. 1-(4-bromophenylsulphonyl)-4-(1-t-butyloxycarbonyl-4-methyl-4-piperidylcarbonyl)piperazine NMR: 1.24 (s, 3H), 1.43 (s, 9H), 2.04 (d, 2H), 2.5 (t, 2H), 3.0 (t, 4H), 3.1–3.26 (m, 2H), 3.54 (d, 2H), 3.73 (t, 4H), 7.65 (dd, 4H).

EXAMPLE 41

A solution of 1-(4-triflouromethylphenylsulphonyl)-4-[1-(6-chloropyrimidin-4-yl)-piperazin-4-ylcarhbonyl]piperidine (20.0 g) in 33% methylamine in ethanol (400 ml) was heated at 110° C. in a Carius tube for 8 hours. The mixture was evaporated to dryness and then dissolved in dichloromethane and washed with saturated aqueous ammonium chloride solution, dried ($Na_2SO_4$) and evaporated. Recrystallisation from methanol/ethyl acetate gave, as a solid 1-(4-triflouromethylphenylsulphonyl)-4-[1-(6-methylaminopyrimidin-4-yl)-piperazin-4-ylcarbonyl]piperidine (13.24 g), mp 237–238° C.

Found C, 51.50; H, 5.10 and N, 16.40%. $C_{22}H_{27}F_3N_6O_3S$ requires C, 51.55; H, 5.31 and N, 16.40%. NMR ($CDCl_3$): 1.80 (m, 2H), 1.95 (m, 2H), 2.55 (m, 3H), 2.90 (d, 3H), 3.50 (m, 4H), 3.65 (m, 4H), 3.80 (m, 2H), 5.40 (s, 1H), 7.80 (d, 2H), 7.90 (d, 2H) and 8.15 (s, 1H); m/z 513 (M+1).

The starting material was prepared as follows:

A solution of 4,6-dichloropyrimidine (10.05 g), tert-butoxycarbonylpiperazine (11.94 g) and triethylamine (28.20 ml) in ethanol (150 ml) was heated at reflux for 18 hours. Solvent was evaporated and the residue dissolved in ethyl acetate and washed with water, saturated aqueous ammonium chloride solution, dried ($Na_2SO_4$) and evaporated. Recrystallisation from ethyl acetate/hexane gave, as a solid 1-(tert-butoxycarbonyl)-4-(6-chloro-pyrimidin-4-yl)piperazine (16.80 g).

NMR ($CDCl_3$): 1.40 (s, 9H), 3.50 (m, 4H), 3.60 (m, 4H), 6.50 (s, 1H), and 8.40 (s, 1H); m/z 298 (M+1).

Ethyl acetate saturated with gaseous HCl was added to a solution of 1-(tert-butoxycarbonyl)-4-(6-chloro-pyrimidin-4-yl)piperazine (16.80 g) in ethyl acetate (50 ml) and the resulting suspension stirred at ambient temperature for 3 hours. Solvent was evaporated to give (6-chloro-pyrimidin-4-yl)piperazine hydrochloride (13.25 g) as a cream solid.

To a solution of N-tert-butoxycarbonyl isonipecotic acid (12.93 g) in tetrahydrofuran (250 ml) at 0° C. was added a solution of carbonyldiimidazole (8.32 g) in tetrahydrofuran (70 ml). The resulting solution was stirred at ambient temperature for 2 hours. This solution was cooled to 0° C. and a solution of (6-chloro-pyrimidin-4-yl)piperazine hydrochloride (13.25 g) and triethylamine (23.57 ml) in dichloromethane (200 ml) added dropwise over 20 minutes. The suspension obtained was stirred at ambient temperature for 18 hours. The mixture was diluted with dichloromethane and washed with water, 2M aqueous citric acid solution, saturated aqueous sodium bicarbonate solution, dried ($Na_2SO_4$) and evaporated to give 1-(tert-butoxycarbonyl)-4-[4-(6-chloro-pyrimidin-4-yl)piperazin-1-ylcarbonyl]piperidine (17.45 g) as a cream solid.

NMR ($CDCl_3$): 1.40 (s, 9H), 1.70 (m, 4H), 2.60 (m, 1H), 2.80 (m, 2H), 3.65 (m, 8H), 4.15 (m, 2H), 6.50 (s, 1H), and 8.40 (s, 1H); m/z 410 (M+1).

Ethyl acetate saturated with gaseous HCl was added to a solution of 1-(tert-butoxycarbonyl)-4-[4-(6-chloro-pyrimidin-4-yl)piperazin-1-ylcarbonyl]piperidine (17.45 g) in ethyl acetate (75 ml) and the resulting suspension stirred at ambient temperature for 3 hours. Solvent was evaporated to give 4-[4-(6-chloro-pyrimidin-4-yl)piperazin-1-ylcarbonyl]hydrochloride (14.72 g) as a cream solid.

NMR (d6-DMSO): 1.70 (m, 4H), 2.90 (m, 3H), 3.20 (m, 2H), 3.40–3.70 (m, 8H, partially obscured by HOD peak) 7.00 (s, 1H), 8.40 (s, 1H); m/z 310 (M+1).

A solution of 4-trifluoromethylbenzenesulphonyl chloride (10.64 g) in dichloromethane (20 ml) was added dropwise over 15 minutes to a mixture of give 4-[4-(6-chloro-pyrimidin-4-yl)piperazin-1-ylcarbonyl] hydrochloride (14.72 g) and triethylamine (29.72 ml) in dichloromethane (200 ml) at 0° C. The solution was stirred at ambient temperature for 18 hours. The solution was diluted with dichloromethane and washed with water, dried ($Na_2SO_4$) and evaporated. The residue was purified by chromatography eluting with 3% methanol in dichloromethane to give 1-(4-triflouromethylphenylsulphonyl)-4-[1-(6-chloro-4-pyrimidyl)-piperazin-4-ylcarbonyl]piperidine(20.05 g) as a solid.

NMR ($CDCl_3$): 1.80 (m, 2H), 1.95 (m, 2H), 2.55 (m, 3H), 3.50–3.80 (m, 10H), 6.50 (s, 1H), 7.80 (d, 2H), 7.90 (d, 2H) and 8.40 (s, 1H); m/z 518 (M+1).

EXAMPLE 42

A solution of phenylsulphonyl chloride (6.71 g) in dichloromethane (20 ml) was added dropwise over 15 minutes to a mixture of 1-(6-methyl-pyrimidin-4-yl)-4-(4-piperidylcarbonyl)piperazine hydrochloride (11.79 g) and triethylamine (25.20 ml) in dichloromethane (100 ml) at 0° C. The solution was stirred at ambient temperature for 18 hours. The solution was diluted with dichloromethane and washed with water, dried ($Na_2SO_4$) and evaporated. The residue was purified by chromatography eluting with 4% methanol in dichloromethane. Recrystallisation from ethyl acetate/hexane gave 1-phenylsulphonyl-4-[1-(6-methyl-pyrimidin-4-yl)-4-piperidylcarbonyl]piperazine (9.40 g) as a solid.

Found C, 58.60; H, 6.40 and N, 16.10 %. $C_{21}H_{27}N_5O_3S$ requires C, 58.72; H, 6.34 and N, 16.30 %. NMR ($CDCl_3$): 1.70 (m, 4H), 2.35 (s, 3H), 2.70 (m, 1H), 3.00 (m, 6H), 3.65 (m, 4H), 4.40 (m, 2H), 6.35 (s, 1H), 7.60 (m, 3H), 7.80 (d, 2H) and 8.50 (s, 1H); m/z 430 (M+1).

The starting material was prepared as follows:

To a solution of N-benzyloxycarbonyl isonipecotic acid (123.64 g) in tetrahydrofuran (300 ml) at 0° C. was added a solution of carbonyldiimidazole (68.80 g) in tetrahydrofuran (500 ml) and dichloromethane (300 ml). The resulting solution was stirred at ambient temperature for 2 hours. This solution was cooled to 0° C. and a solution of 1-(tert-butoxycarbonyl)piperazine (87.02 g) in tetrahydrofuran (200 ml) added dropwise over 20 minutes. The suspension obtained was stirred at ambient temperature for 48 hours. Solvent was evaporated. The residue was dissolved in diethyl ether/dichloromethane (1500 ml) and washed with water, 2M aqueous citric acid solution, saturated aqueous sodium bicarbonate solution, dried ($Na_2SO_4$) and evaporated to give 1-(tert-butoxycarbonyl)-4-[1-(benzyloxycarbonyl)-4-piperidylcarboyl]piperazine (180.00 g) as a solid.

NMR ($CDCl_3$): 1.45 (s, 9H), 1.75 (m, 4H), 2.60 (m, 1H), 2.85 (m, 2H), 3.40 (m, 6H), 3.60 (m, 2H), 4.20 (m, 2H), 5.10 (s, 2H), and 7.35 (m, 5H); m/z 432 (M+1).

A solution of 1-(tert-butoxycarbonyl)-4-[1-benzyloxycarbonyl-4-piperidylcarbonyl]piperazine (41.31 g) in ethanol (1200 ml) was hydrogenated over 10% palladium on carbon for 18 hours. The reaction mixture was filtered through celite and solvent evaporated to give, 1-(tert-hutoxycarbonyl) -4-(4-piperidylcarbonyl) piperazine (18.95 g) as a solid.

NMR ($CDCl_3$): 1.45 (s, 9H), 1.70 (m, 4H), 2.60 (m, 2H), 2.80 (m, 1H), 3.50 (m, 10H); m/z 298

A solution of 6-methyl-2,4-dichloropyrimidine (10.26 g), 1-(tert-butoxycarbonyl)-4-(4-piperidylcarbonyl) (18.71 g) and triethylamine (26.30 ml) in ethanol (300 ml) was heated at reflux for 8 hours. Solvent was evaporated and the residue dissolved in ethyl acetate and washed with water, dried ($Na_2SO_4$) and evaporated. The residue was purified by chromatography eluting with ethyl acetate to give, as a solid 1-(tert-butoxycarbonyl)-4-[1-(2-chloro-6-methylpyrimidin-4-yl)-4-piperidylcarbonyl] piperazine (15.37 g).

NMR ($CDCl_3$): 1.45 (s, 9H), 1.80 (m, 4H), 2.35 (s, 3H), 2.80 (m, 1H), 3.50 (m, 10H), 4.40 (m, 2H) and 6.25 (s, 1H); m/z 424 (M+1).

A solution of 1-(tert-butoxycarbonyl)-4-[1-(2-chloro-6-methyl-pyrimidin-4-yl)-4-piperidylcarbonyl]piperazine (15.37 g) in ethanol (350 ml) was hydrogenated over 10% palladium on carbon for 18 hours. The reaction mixture was filtered through celite and solvent evaporated to give, as a solid 1-(tert-butoxycarbonyl)-4-[1-(6-methylpyrimidin-4-yl)-4-piperidylcarbonyl] piperazine (14.07 g).

NMR ($CDCl_3$): 1.45 (s, 9H), 1.90 (m, 4H), 2.60 (s, 3H), 2.95 (m, 1H), 3.50 (m, 12H), 6.50 (s, 1H) and 8.50 (s, 1H); m/z 390 (M+1).

Ethyl acetate saturated with gaseous HCl was added to a solution of 1-(tert-butoxycarbonyl)-4-[1-(6-methylpyrimidin-4-yl)-4-piperidylcarbonyl] piperazine (14.07 g) in ethyl acetate (50 ml) and the resulting suspension stirred at ambient temperature for 3 hours. Solvent was evaporated to give 4-[1-(6-methylpyrimidin-4-yl)-4-piperidylcarbonyl] piperazine hydrochloride (11.79 g) as a solid.

NMR (d6-DMSO): 1.50 (m, 2H), 1.80 (m, 2H), 2.40 (s, 3H), 3.05 (m, 8H), 3.30 (m, 1H), 3.65 (m, 4H), 3.80 (m, 4H), 7.15 (s, 1H) and 8.70 (s, 1H); m/z 290 (M+1).

EXAMPLE 43

A solution of 1-(4-triflouromethylphenylsulphonyl)-4-[1-(6-chloro-pyrimidin-4-yl)piperazin-4-ylcarbonyl]piperazine (26.0 g) in 33% methylamine in ethanol (400 ml) was heated at 110° C. in a Carius tube for 8 hours. The mixture was evaporated to dryness and the residue recrystallised from methanol to give, as a solid 1-(4-triflouromethylphenylsulphonyl)-4-[1-(6-metliylamino-pyrimidin-4-yl)piperazin-4-ylcarbonyl]piperazine (13.67 g), mp 230–231° C. Found C, 49.10; H, 4.90 and N, 19.00%. $C_{21}H_{26}F_3N_7O_3S$ requires C, 49.12; H, 5.10 and N, 19.09% NMR ($CDCl_3$): 2.85 (d, 3H), 3.10 (m, 4H), 3.30 (m, 4H), 3.40 (m, 4H), 3.60 (m, 4H), 4.75 (m, 1H), 5.40 (s, 1H), 7.80 (d, 2H), 7.90 (d, 2H) and 8.15 (s, 1H); m/z 154 (M+1).

The starting material was prepared as follows:

To a solution of tert-butoxycarbonyl piperazine (37.20 g) and triethylamine (39.00 ml) in dichloromethane (750 ml) at 3° C. was added a solution of 4-nitrophenylchloroformate (42.30 g) in dichloromethane (200 ml) dropwise over 1 hour and the resulting yellow solution stirred at room temperature for 3 hours. The solution was washed with 1M aqueous citric acid solution, water, dried ($Na_2SO_4$) and evaporated. Recrystallisation from ethyl acetate/hexane gave, as a colourless solid 1-(tert-butoxycarbonyl)-4-(4-nitrophenoxy) carbonylpiperazine (60.50 g).

NMR ($CDCl_3$): 1.45 (s, 9H), 3.60 (m, 8H), 7.25 (d, 2H) and 8.20 (d, 2H).

A solution of 1-(tert-butoxycarbonyl)-4-(4-nitrophenoxy) carbonylpiperazine (42.05 g), piperazine (61.82 g) in tetrahydrofuran (200 ml) was heated at reflux for 18 hours. Solvent was evaporated and dichloromethane added to the residue. The mixture was filtered and the filtrate washed with saturated aqueous sodium carbonate solution, water, dried ($Na_2SO_4$) and evaporated to give, as a pale yellow solid 1-[1-(tert-butoxycarbonyl)-piperazin-4-ylcarhboniyl] piperazine (33.75 g).

NMR ($CDCl_3$): 1.45 (s, 9H), 2.85 (m, 4H), 3.20 (m, 8H) and 3.40 (m, 4H); m/z 299 (M+1).

A solution of 4,6-dichloropyrimidine (8.60 g), 1-[1-(tert-butoxycarbonyl)-piperazin-4-ylcarbonyl]piperazine 15.64 g) and triethylamine (21.95 ml) in ethanol (300 ml) was stirred at room temperature for 30 minutes. Solvent was evaporated and the residue dissolved in dichloromethane and washed with water, saturated aqueous sodium chloride solution, dried ($Na_2SO_4$) and evaporated to give, as a pale yellow solid 1-[1-(tert-butoxycarbonyl)-piperazin-4-ylcarbonyl]-4-(6-chloro-pyrimidin-4-yl) piperazine (21.20 g).

NMR ($CDCl_3$): 1.45 (s, 9H), 3.25 (m, 4H), 3.40 (m, 4H), 3.45 (m, 4H), 3.70 (m, 4H), 6.50 (s, 1H) and 8.40 (s, 1H); m/z 411 (M+1).

Ethyl acetate saturated with gaseous HCl was added to a solution of 1-[1-(tert-hutoxycarbonyl)-piperazin-4-ylcarbonyl]-4-(6-chloro-pyrimidin-4-yl) piperazine (21.20 g) in ethyl acetate (75 ml) and the resulting suspension stirred at ambient temperature for 3 hours. Solvent was evaporated to give 4-[1-(6-chloro-pyrimidin-4-yl)piperazin-4-ylcarbonyl]piperazine hydrochloride (13.25 g) as a pale yellow solid.

NMR (d6-DMSO): 3.00 (m, 4H), 3.25 (m, 4H), 3.40 (m, 4H), 3.60 (m, 4H), 7.00 (s, 1H), and 8.40 (s, 1H).

A solution of 4-triflouromethylphenylsulphonyl chloride (13.25 g) in dichloromethane (30 ml) was added dropwise over 15 minutes to a mixture of 4-[1-(6-chloro-pyrimidin-4-yl)piperazin-4-ylcarbonyl]piperazine (21.50 g) and triethylamine (43.13 ml) in dichloromethane (270 ml) at 0° C. The solution was stirred at ambient temperature for 18 hours. The solution was diluted with dichloromethane and washed with water, dried ($Na_2SO_4$) and evaporated to give 1-(4-triflouromethylphenylsulphonyl)-4-[1-(6-chloro-pyrimidin-4-yl)piperazin-4-ylcarbonyllpiperazine (26.0 g) as a solid.

NMR ($CDCl_3$): 3.10 (m, 4H), 3.30 (m, 4H), 3.40 (m, 4H), 3.60 (m, 4H), 6.50 (s, 1H), 7.80 (d, 2H), 7.90 (d, 2H) and 8.40 (s, 1H); m/z 519 (M+1).

EXAMPLE 44

A solution of 1-(4-bromophenylsulphonyl)-4-[1-(6-chloropyrimidin-4-yl)-piperazin-4-ylcarbonyl]piperazine (1.20 g) in 33% methylamine in ethanol (35 ml) was heated at 110° C. in a Carius tube for 16 hours. The mixture was evaporated to dryness and then dissolved in dichloromethane and washed with saturated aqueous ammonium chloride solution, dried ($Na_2SO_4$) and evaporated. The residue was recrystallised from methanol/ethyl acetate to give, as a solid 1-(4-bromophenylsulphonyl)4-[1-(6-methylaminopyrimidin-4-yl)-piperazin-4-ylcarbonyl] piperazine (0.65 g), mp 219–221° C. Found C, 45.80; H, 5.10 and N, 18.50%. $C_{20}H_{26}BrN_7O_3S$ requires C, 45.80; H, 5.00 and N, 18.70% NMR ($CDCl_3$): 2.85 (d, 3H), 3.00 (m, 4H), 3.30 (m, 4H), 3.40 (m, 4H), 3.60 (m, 4H). 4.75 (m, 1H), 5.40 (s, 1H), 7.60 (d, 2H), 7.70 (d, 2H) and 8.15 (s, 1H); m/z 524 (M+1).

The starting material were prepared in an analogous way as described in Example 53. The following intermediate was isolated:

1-(4-hrl)mohenzenesulphonyl)-4-[1-(6-chloropyrimidin-4-yl)-piperazin-4-ylcarbonyl]piperazine (36.69 g) as a solid.

NMR ($CDCl_3$): 3.05 (m, 4H), 3.30 (m, 4H), 3.40 (m, 4H), 3.65 (m, 4H), 6.50 (s, 1H), 7.10 (d, 2H). 7.20 (d, 2H) and 8.40 (s, 1H); m/z 529 (M+1).

EXAMPLE 45

A solution of 1-(4-bromophenylsulphonyl)-4-[1-(6-chloro-pyrimidin-4-yl)-piperidin-4-yl)-piperidin-4-ylcarbonyl]piperazine (3.00 g) in 33% methylamine in ethanol (70 ml) was heated at 110° C. in a Carius tube for 16 hours. The mixture was evaporated to dryness and then dissolved in dichloromethane and washed with saturated aqueous ammonium chloride solution, dried ($Na_2SO_4$) and evaporated. The residue was recrystallised from methanol/ethyl acetate to give, as a solid 1-(4-bromophenylsulphonyl)-4-1-(6-methylamino-pyrimidin-4-yl)-piperidin-4-yicarbonyl]piperazine (2.43 g), mp 214–215° C. Found C, 48.40; H, 5.20 and N, 16.10%. $C_{21}H_{27}BrN_6O_3S$ requires C, 48.19; H, 5.20 and N, 16.05%. NMR ($CDCl_3$): 1.70 (m, 4H), 2.35 (m, 1H), 2.85 (d, 3H), 3.00 (m, 6H), 3.65 (m, 4H), 4.35 (m, 2H), 4.65 (m, 1H), 5.40 (s, 1H), 7.60 (d, 2H), 7.70 (d, 2H) and 8.15 (s, 1H); m/z 523 (M+1).

The starting material was prepared as follows:

To a solution of N-benzyloxycarbonyl isonipecotic acid (123.64 g) in tetrahydrofuran (300 ml) at 0° C. was added a solution of carbonyldiimidazole (68.80 g) in tetrahydrofuran (500 ml) and dichloromethane (300 ml). The resulting solution was stirred at ambient temperature for 2 hours. This solution was cooled to 0° C. and a solution of 1-(tert-butoxycarbonyl)piperazine (87.02 g) in tetrahydrofuran (200 ml) added dropwise over 20 minutes. The suspension obtained was stirred at ambient temperature for 48 hours. Solvent was evaporated. The residue was dissolved in diethyl ether/dichloromethane (1500 ml) and washed with water, 2M aqueous citric acid solution, saturated aqueous sodium bicarbonate solution, dried ($Na_2SO_4$) and evaporated to give 1-(tert-butoxycarbonyl)-4-[1-(benzyloxycarbonyl)4-piperidylcarbonyl]piperazine (180.00 g) as a solid.

NMR ($CDC_3$): 1.45 (s, 9H), 1.75 (m, 4H), 2.60 (m, 1H), 2.85 (m, 2H), 3.40 (m, 6H), 3.60 (m, 2H), 4.20 (m, 2H), 5.10 (s, 2H), and 7.35 (m, 5H); m/z 432 (M+1).

A solution of 1-(tert-butoxycarbonyl)-4-[1-(benzyloxycarbonyl)-4-piperidylcarbonyl]piperazine (41.31 g) in ethanol (1200 ml) was hydrogenated over 10% palladium on carbon for 18 hours. The reaction mixture was filtered through celite and solvent evaporated to give, 1-(tert-butoxycarbonyl)-4-(piperidin-4-ylcarbonyl) piperazine (18.95 g) as a solid.

NMR ($CDCl_3$): 1.45 (s, 9H), 1.70 (m, 4H), 2.60 (m, 2H), 2.80 (m, 1H), 3.50 (m, 10H); m/z 298

A solution of 4,6-dichloropyrimidine (3.60 g), 1-(tert-butoxycarbonyl)-4-(-4-piperidylcarbonyl)piperazine (6.00 g) and sodium hydrogen carbonate (4.20 g) in ethanol (100 ml) was heated at reflux for 6 hours. Solvent was evaporated and the residue dissolved in ethyl acetate and washed with water, dried ($Na_2SO_4$) and evaporated. The residue was recrystallised from ethyl acetate to give, as a solid 1-(tert-butoxycarbonyl)-4-[1-(6-chloro-pyrimidin-4-yl)-piperidin-4-ylcarbonyl]piperazine (7.40 g).

NMR (CDCl$_3$): 1.45 (s, 9H), 1.80 (m, 4H), 2.80 (m, 1H), 3.10 (m, 2H), 3.50 (m, 8H), 4.40 (m, 2H), 6.50 (s, 1H) and 8.40 (s, 1H); m/z 410 (M+1).

Ethyl acetate saturated with gaseous HCl was added to a solution of 1-(tert-butoxycarbonyl)-4-[1-(6-chloro-pyrimidin-4-yl)-piperidin-4-ylcarbonyl]piperazine (7.40 g) in ethyl acetate (30 ml) and the resulting suspension stirred at ambient temperature for 3 hours. Solvent was evaporated to give 1-[1-(6-chloro-pyrnmidin-4-yl)-4-piperidylcarbonyl] hydrochloride (7.10 g) as a solid.

NMR (d6-DMSO): 1.40 (m, 2H), 1.7 (m, 2H), 3.00 (m, 7H), 3.70 (m, 4H), 4.40 (m, 2H), 6.95 (2, 1H) and 8.30 (s, 1H).

4-Bromophenylsulphonyl chloride (2.77 g) was added to a mixture 1-[1-(6-chloro-pyrimidin-4-(yl)-4-piperidylcarbonyl] hydrochloride (5.20 g) and triethylamine (10.10 ml) in dicliloromethane (200 ml) at 0° C. The solution was stirred at ambient temperature for 18 hours. The solution was diluted with dichloromethane and washed with water, dried (Na$_2$SO$_4$) and evaporated. The residue was purified by chromatography eluting with 1.5% methanol in dichloromethane to give 1-(4-bromobenzenesulphonyl)-4-[1-(6-chloro-pyrimidin-4-yl)-4-piperidylcarhonyl] piperazine (2.00 g) as a solid.

NMR (CDCl$_3$): 1.80 (m, 4H), 2.70) (m, 1H), 3.00 (m, 6H), 3.65 (m, 4H), 4.35 (m, 2H), 6.50 (s, 1H), 7.60 (d, 2H), 7.70 (d, 2H) and 8.40 (s, 1H); m/z 528 (M+1).

EXAMPLE 46

A solution of 1-(4-trifluoromethylphenylsulphonyl)-4-[1-(6-chloro-pyrimidin-4-yl)-4-piperidylcarbonyl]piperazine (1.80 g) in 33% methylamine in ethanol (70 ml) was heated at 110° C. in a Carius tube for 16 hours. The mixture was evaporated to dryness and then dissolved in dichloromethane and washed with saturated aqueous ammonium chloride solution, dried (Na$_2$SO$_4$) and evaporated. The residue was recrystallised from methanol/ethyl acetate to give, as a solid 1-(4-trifluoromethylphenylsulphonyl)-4-[1-(6-methylamino-pyrimidin-4-yl)-4-piperidylcarhonyl] piperazine (1.26 g), mp 237–239° C.

Found C, 51.70; H, 5.30 and N, 16.30 %. C$_{22}$H$_{27}$F$_3$N$_6$O$_3$S requires C, 51.55; H, 5.30 and, N, 16.40%. NMR (CDCl$_3$): 1.70 (m, 4H), 2.60 (m, 1H), 2.85 (d, 3H), 2.90 (m, 2H), 3.10 (m, 4H), 3.65 (m, 4H), 4.35 (m, 2H), 4.65 (m, 1H), 5.40 (s, 1H), 7.80 (d, 2H), 7.90 (d, 2H) and 8.15 (s, 1H): m/z 513 (M+1).

The starting material were prepared as by the methods described in Example 55, and the following intermediates were isolated:

4-Trifluoromethylphenylsulphonyl chloride (1.32 g) was added to a mixture 1-[1-(6-chloro-pyrimidin-4-yl)-4-piperidylcarbonyl]piperazine hydrochloride (2.60 g) and triethylamine (5.00 ml) in dichloromethane (100 ml) at 0° C. The solution was stirred at ambient temperature for 18 hours. The solution was diluted with dichloromethane and washed with water, dried (Na$_2$SO$_4$) and evaporated. The residue was purified by chromatography eluting with 1.5% methanol in dichloromethane to give 1-(4-trifluoromethylphenylsulphonyl)-4-[1-(6-chloro-pyrimidin-4-yl)-4-piperidylcarbonyl]piperazine (1.80 g) as a solid.

NMR (CDCl$_3$): 1.80 (m, 4H), 2.70 (m, 1H), 3.00 (m, 6H), 3.70 (m, 4H), 4.35 (m, 2H), 6.50 (s, 1H), 7.80 (d, 2H), 7.90 (d, 2H) and 8.40 (s, 1H); m/z 518 (M+1).

EXAMPLE 47

To a white suspension of 1-(2-ethylpyrimidin-4-yl)-piperazine dihydrochloride (3g, 10.362 mmol) in DMF (70 ml) and triethylamine (4.194 g/5.77 ml/1.449 mmol) at room temperature as added 1-(4-bromophenylsulphonyl)-4-(4-nitrophenyloxycarbonyl)-piperazine (5.625 g, 10.363 mmol). This solution as allowed to stir for 16 hours at 100° C. DMF was evaporated. Water (250 ml and dichloromethane (250 ml) were added, the mixture basified with NaOH. The organic phase was repeatedley washed with water. The organic was dried and evaporated. The residue was purified by "flash" chromatography on silica gel using metlhanol:dichloromethane (0 to 100%) as eluent to give a light brown solid. Trituration with ether (100 (ml) gave 1-(bromophenylsulphonyl)-4-[1-(2-ethylpyrimidin-4-yl) piperazin-4-ylcarbonyl]piperazine as a light brown solid (3.555g): MP 155–156° C.

NMR (CDCL$_3$): 1.25 (t, 3H), 2.75 (q, 2H), 3.05 (t, 4H), 3.32 (t, 4H), 3.40 (t, 4H), 3.65 (t, 4H), 6.30 (d, 1H), 7.66 (d, 2H), 7.70 (d, 2H), 8.20 (d, 1H),:ESP$^+$-MS m/z 524 (M+H)

EXAMPLE 48

Illustrative pharmaceutical dosage forms suitable for presenting the compounds of the invention fo)r therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium Stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| (c) Tablet III | mg/tablet |
|---|---|
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Compound Z* | 10 |
| Lactose Ph. Eur. | 488.5 |
| Magnesium stearate | 1.5 |

Note

The active ingredient Compound Z is a compound of formula I, or a salt thereof, for example a compound of formula I described in any of the preceding Examples. The tablet compositions (a)–(c) may be enteric coated by conventional means, for example, with cellulose acetate phthalate.

Formulae

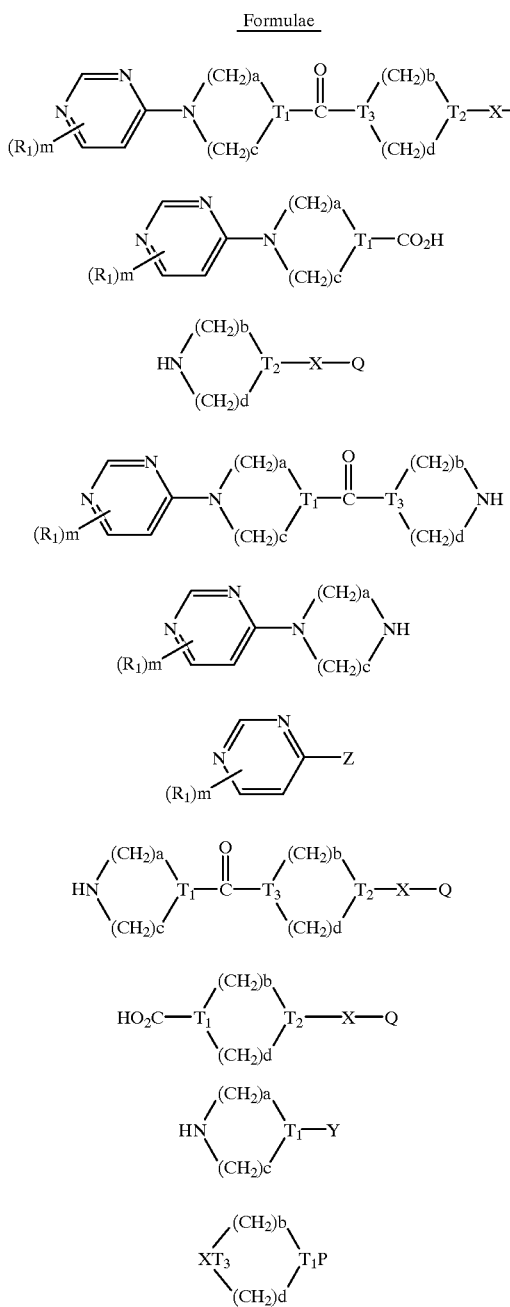

What is claimed is:

1. A compound of formula I, or a pharmaceutically acceptable salt thereof;

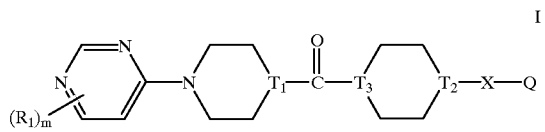

wherein
$T^1$ is selected from N and CH;
$R^1$ is hydrogen, amino, halogeno, cyano, (1–6C)alkyl or (1–6C)alkoxy;
m is 1 or 2;
$T^2$ is selected from CH and N;
$T^3$ is selected from N and CH provided that when $T^2$ is CH then $T^3$ is not CH and
when $T^1$ is CH then $T^3$ is not CH;
wherein the heterocyclic ring containing $T^1$ and the heterocyclic ring containing $T^2$ may, independently, be optionally substituted by one or more substituents selected from (1–6C) alkyl, (1–6C)alkoxy, phenyl(1–4C)alkyl, halogeno and (1–6C)alkoxycarbonyl;
X is selected from O, CO, S, SO, $SO_2$ and $CH_2$;
Q is phenyl and wherein Q is substituted by one or two substituents independently selected from halogeno and (1–6C)alkyl.

2. A compound of formula I as claimed in claim 1 wherein $T^1$, $T^2$ and $T^3$ are N.

3. A compound of formula I as claimed in claims 1 or 2 wherein $R^1$ is selected from hydrogen, amino, (1–6C) alkyl and halogeno.

4. A compound of formula I as claimed in claims 1 or 2 wherein $R^1$ is selected from hydrogen, amino, methyl and chloro.

5. A compound of formula I as claimed in claim 4 wherein m is 1 and $R^1$ is methyl.

6. A compound of formula I as claimed in claims 1 or 2 wherein the heterocyclic ring containing $T^1$ and $T^2$ is unsubstituted.

7. 1-(4-Bromophenylsulphonyl)-4-[1-(6-methylpyrimidin-4-yl)piperazin-4-ylcarbonyl]piperazine.

8. A pharmaceutical composition comprising a compound of formula I as claimed in claims 1 or 7 or a pharmaceutically acceptable salt thereof and a pharmaceutically acceptable diluent or carrier thereto.

9. A method of lowering the level of cholesterol in blood which comprises the administration of a compound of formula I or a pharmaceutically acceptable salt thereof,

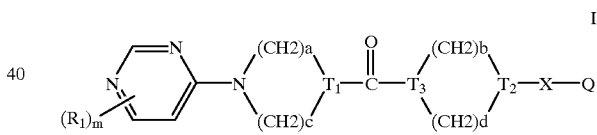

wherein
$T^1$ is selected from N and CH;
$R^1$ is hydrogen, amino, halogeno, cyano, (1–6C)alkyl or (1–6C)alkoxy;
m is 1 or 2;
$T^2$ is selected from CH and N;
$T^3$ is selected from N and CH provided that when $T^2$ is CH then $T^3$ is not CH and when $T^1$ is CH then $T^3$ is not CH;
a and b are 2;
c and d are 2;
wherein the heterocyclic ring containing $T^1$ and the heterocyclic ring containing $T^2$ may, independently, be optionally substituted by one or more substituents selected from (1–6C)alkyl, (1–6C)alkoxy, phenyl (1–4C)alkyl, halogeno and (1–6C)alkoxycarbonyl;
X is selected from O, CO, S, SO, $SO_2$ and $CH_2$;
Q is selected from phenyl, naphthyl, phenyl(2–6C)alkenyl and a heteroaryl moiety which comprises a 5- or 6-membered monocyclic heteroaryl ring containing up to 3 heteroatoms selected from the group consisting of oxygen, nitrogen and sulphur and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, -(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C) alkanoyl and tetrazolyl.

10. A method of inhibiting oxido-squalene cyclase in a warm-blooded animal requiring such treatment which method comprises administering to said animal an effective amount of a compound of formula I as claimed in claim 1, or a pharmaceutically acceptable salt thereof.

11. A method of inhibiting oxido-squalene cyclase in a warm-blooded animal requiring such treatment which method comprises administering to said animal an effective amount of a compound of formula I or a pharmaceutically acceptable salt thereof,

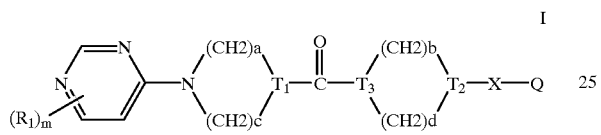

wherein $T^1$ is selected from N and CH;

$R^1$ is hydrogen, amino, halogeno, cyano, (1–6C)alkyl or (1–6C)alkoxy;

m is 1 or 2;

$T^2$ is selected from CH and N;

$T^3$ is selected from N and CH provided that when $T^2$ is CH then $T^3$ is not CH and when $T^1$ is CH then $T^3$ is not CH;

a and b are 2;

c and d are 2;

wherein the heterocyclic ring containing $T^1$ and the heterocyclic ring containing $T^2$ may, independently, be optionally substituted by one or more substituents selected from (1–6C)alkyl, (1–6C)alkoxy, phenyl (1–4C)alkyl, halogeno and (1–6C)alkoxycarbonyl;

X is selected from O, CO, S, SO, $SO_2$ and $CH_2$;

Q is selected from phenyl, naphthyl, phenyl(2–6C)alkenyl and a heteroaryl moiety which comprises a 5- or 6-membered monocyclic heteroaryl ring containing up to 3 heteroatoms selected from the group consisting of oxygen, nitrogen and sulphur and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalky, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl and tetrazolyl.

* * * * *